(12) United States Patent
Bonner-Weir et al.

(10) Patent No.: US 9,328,331 B2
(45) Date of Patent: May 3, 2016

(54) COMPOSITIONS AND METHODS FOR PROMOTING BETA CELL MATURITY

(75) Inventors: Susan Bonner-Weir, Cambridge, MA (US); Arun Sharma, Cambridge, MA (US); Cristina Aguayo-Mazzucato, Mexico City (MX)

(73) Assignee: Joslin Diabetes Center, Inc., Boston, MA (US)

( * ) Notice: Subject to any disclaimer, the term of this patent is extended or adjusted under 35 U.S.C. 154(b) by 7 days.

(21) Appl. No.: 13/321,538

(22) PCT Filed: May 21, 2010

(86) PCT No.: PCT/US2010/035762
§ 371 (c)(1),
(2), (4) Date: Feb. 6, 2012

(87) PCT Pub. No.: WO2010/135639
PCT Pub. Date: Nov. 25, 2010

(65) Prior Publication Data
US 2012/0141436 A1    Jun. 7, 2012

Related U.S. Application Data

(60) Provisional application No. 61/180,364, filed on May 21, 2009.

(51) Int. Cl.
| | | |
|---|---|---|
| *A61P 3/10* | (2006.01) | |
| *A61K 35/12* | (2015.01) | |
| *C12N 5/02* | (2006.01) | |
| *C12N 5/071* | (2010.01) | |
| *C07K 14/62* | (2006.01) | |

(52) U.S. Cl.
CPC .............. *C12N 5/0676* (2013.01); *C07K 14/62* (2013.01); *C12N 2501/395* (2013.01)

(58) Field of Classification Search
None
See application file for complete search history.

(56) References Cited

U.S. PATENT DOCUMENTS 6,436,704 B1 * 8/2002 Roberts et al. ............... 435/366
2007/0081980 A1    4/2007 Jin

FOREIGN PATENT DOCUMENTS

WO    WO 03100026 A2 * 12/2003
WO    WO 03100038 A1 * 12/2003

OTHER PUBLICATIONS

Rawdon, BB; Andrew, A; "Effects of tri-iodothyronine (T3), insulin, insulin-like growth factor I (IGF-I) and transforming growth factor beta1 (TGFb1) on the proportion of insulin cells in cultured embryonic chick pancreas" Analytical Embryology, 198, 245-254, 1998.*
Zhang, Chuan; et al; "MafA Is a Key Regulator of Glucose-Stimulated Insulin Secretion" Molecular and Cell Biology, 25, 4969-4976, 2005.*
Luo, L-G, et al., "Thyrotropin Releasing Hormone (TRH) may preserve pancreatic islet cell function: potential role in the treatment of diabetes mellitus," ACTA Biomed 78(1): 216-221 (2007).
Mukhi, S. et al., "Remodeling of insulin producing beta cells during Xenopus laevis metamorphosis," Dev. Biol. 328 (2): 384-91 (2009).

* cited by examiner

*Primary Examiner* — Renee Claytor
*Assistant Examiner* — David Berke-Schlessel
(74) *Attorney, Agent, or Firm* — Pierce Atwood LLP; Kevin M. Farrell; David J. Wilson

(57) ABSTRACT

Compositions and methods for providing an enriched population of mature, glucose-responsive insulin secreting cells, and for modulating insulin expression, activity and secretion in a subject.

10 Claims, 13 Drawing Sheets

COMPOSITIONS AND METHODS FOR PROMOTING BETA CELL MATURITY

CLAIM OF PRIORITY

This application is the U.S. National Stage of International Application No. PCT/US2010/035762, filed on May 21, 2010, published in English, which claims priority under 35 USC §119(e) to U.S. Patent Application Ser. No. 61/180,364, filed on May 21, 2009, the entire contents of which are hereby incorporated by reference.

FEDERALLY SPONSORED RESEARCH OR DEVELOPMENT

This invention was made with Government support under Grant Nos. DK066056 and DK 60127 awarded by National Institute of Health (NIH). The Government has certain rights in the invention.

TECHNICAL FIELD

This disclosure relates to cell therapy methods, and more particularly to compositions and methods for promoting beta cell maturity.

BACKGROUND

Cell therapy is emerging as an increasingly important technique for the treatment of diabetes and other conditions in which a reduction in pancreatic beta cell number or beta cell function is causative or contributory. In vitro, insulin producing (e.g., expressing) beta cells can be derived from various sources (e.g., human embryonic stem cells), but in general these cells are immature in their response to glucose, and although the cells contain and express insulin, they fail to secrete insulin in the presence of glucose or in response to changes in glucose concentration, as seen in recent publications (D'Amour et al., Nature Biotech., 24:1392-1401, 2006; Kroon et al., Nature Biotech., 26:443-452, 2008). Thus, renewable sources of beta cells that express insulin and secrete insulin in response to glucose are required for transplantation in cell therapy for diabetes.

SUMMARY

Described herein are methods for providing enriched populations of mature, glucose-responsive insulin secreting cells. The methods include providing an initial isolated population of insulin-expressing cells (e.g., a substantially enriched population), wherein the cells do not substantially secrete insulin in response to glucose; and contacting the initial population of cells with triiodothyronine (T3) thyroid hormone or an analog thereof under conditions and for a time sufficient to induce maturation of at least some of the cells into mature cells that secrete insulin in the presence of glucose, thereby providing an enriched population of mature, glucose-responsive insulin secreting cells.

Thus, in one aspect, the invention provides methods for providing an enriched population of mature, glucose-responsive insulin secreting cells. The methods include providing an initial population of insulin-expressing immature beta cells, wherein the cells do not substantially secrete insulin in response to glucose; and contacting the initial population of immature beta cells with triiodothyronine (T3) thyroid hormone or an analog thereof under conditions and for a time sufficient to induce maturation of at least some of the cells into mature cells that secrete insulin in the presence of glucose, thereby providing an enriched population of mature, glucose-responsive insulin secreting cells.

In another aspect, the invention provides methods for providing an enriched population of mature, glucose-responsive insulin secreting cells. The methods include providing an initial population of insulin-expressing immature beta cells, wherein the cells secrete a first level of insulin in the presence of glucose; contacting the initial population of cells with triiodothyronine (T3) thyroid hormone or an analog thereof under conditions and for a time sufficient to induce maturation of at least some of the cells into mature cells that secrete a second level of insulin in the presence of glucose, wherein the second insulin level is greater than the first level, thereby providing an enriched population of mature, glucose-responsive insulin secreting cells.

In some embodiments, the initial population of insulin-expressing cells is provided by a method including providing a stem cell or a beta cell progenitor; and differentiating the stem cell or progenitor cell into a population comprising insulin-expressing cells. In some embodiments, the stem cell or β cell progenitor is an iPS cell or embryonic stem cell.

In some embodiments, the initial population of insulin-expressing cells secretes substantially no insulin in a glucose responsive manner.

In some embodiments, the initial population of insulin-expressing immature beta cells secretes substantially less insulin in a glucose responsive manner than is secreted by a comparable population of mature beta cells.

In some embodiments, the initial population of insulin-expressing cells expresses insulin, but does not substantially express MafA.

In some embodiments, the initial population of insulin-expressing cells is an enriched population of immature beta cells.

In some embodiments, the analog of T3 is selected from the group consisting of T4 thyroid hormone (e.g., thyroxine or L-3,5,3',5'-tetraiodothyronine), selective and non-selective thyromimetics, TRbeta selective agonist-GC-1, GC-24, 4-Hydroxy-PCB 106, MB07811, MB07344,3,5-diiodothyropropionic acid (DITPA); the selective TR-beta agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy] acetic acid (GC-1), 3,5-dichloro-4-[(4-hydroxy-3-isopropylphenoxy)phenyl]acetic acid (KB-141), and 3,5-diiodothyropropionic acid (DITPA).

In some embodiments, the initial population of insulin-expressing cells express one or more, two or more, three or more, or all four of surfactant protein-D (SPD; also known as SFTPD), matrix metalloproteinase 2 (MMP2), Frizzled2 (Friz2) and/or cytokeratin 19 (CK19, also known as keratin 19 or KRT19).

In a further aspect, the invention provides methods for treating or reducing the risk of developing diabetes in a subject, by administering to a subject an enriched population of mature, glucose-responsive insulin secreting cells produced by a method described herein.

DEFINITIONS

As used herein "target cell" and "target cells" refer to immature beta cells.

As used herein, expression refers to mRNA levels and/or protein levels. Oligonucleotides suitable to detect mRNA, e.g., using RT-PCR, can be designed using techniques routine in the art. Alternatively or in addition, protein expression can be assessed using any art recognized technique (e.g., any antibody based detection technique).

As used herein, the term "treatment," when used in the context of a therapeutic strategy to treat a disease or disorder (e.g., cell therapy), means any manner in which one or more of the symptoms of a disease or disorder are ameliorated or otherwise beneficially altered. As used herein, amelioration of the symptoms of a particular disease or disorder refers to any lessening, whether permanent or temporary, lasting or transient that can be attributed to or associated with treatment by the compositions and methods of the present invention. This definition of the term "treatment" does not apply in the context of an in vitro method for promoting beta cell maturity.

The terms "effective amount" and "effective to treat," as used herein, refer to an amount or a concentration of one or more compounds or a pharmaceutical composition described herein utilized for a period of time (including in vitro and in vivo acute or chronic administration and periodic or continuous administration) that is effective within the context of its administration for causing an intended effect or physiological outcome.

Effective amounts of one or more compounds or a pharmaceutical composition for use in the present invention include amounts that promote beta cell maturity, e.g., an increase in glucose-dependent insulin secretion in a cell or an increase in the level of MafA in a cell.

The term "subject" is used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, experimental animals, farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
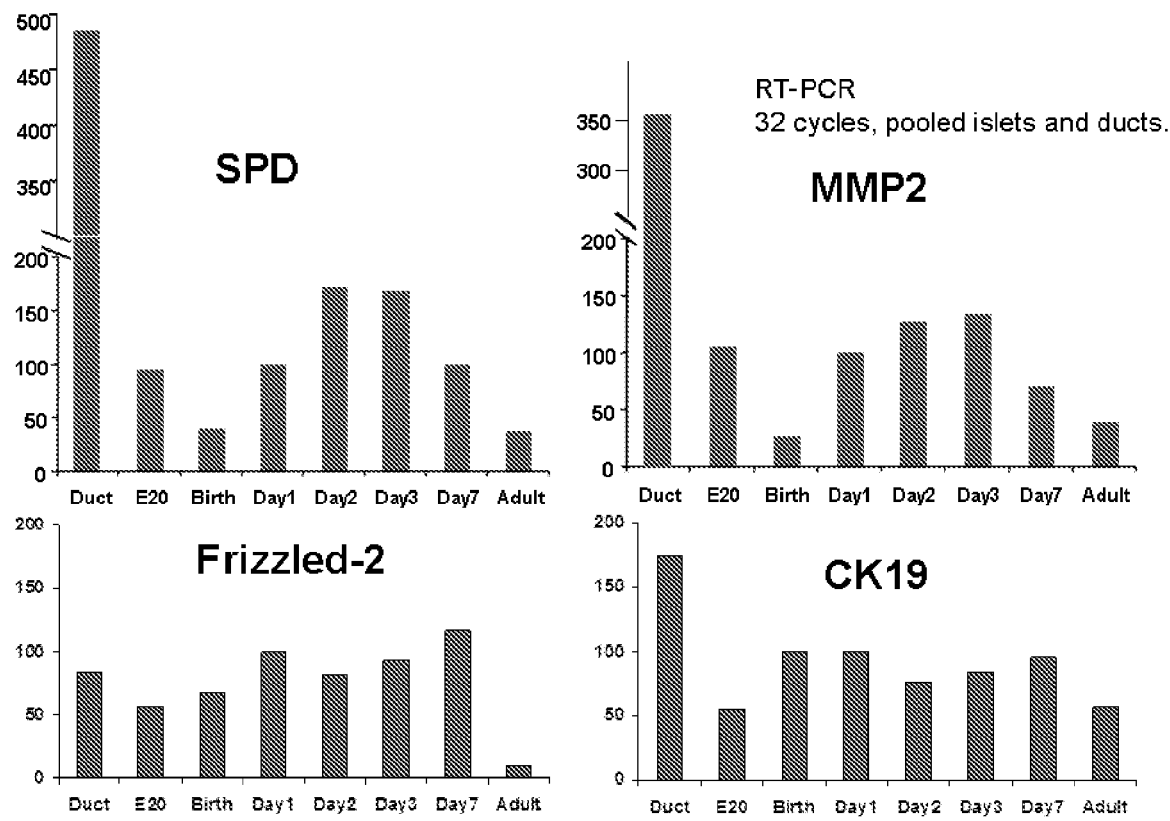
FIG. 1 is a histogram showing surfactant protein-D (SPD), matrix metalloproteinase 2 (MMP2), Frizzled2 (Friz2) and cytokeratin 19 (CK19) expression levels in beta cells at various stages of neonatal development.

The present disclosure is based, at least in part, on the surprising discovery that immature beta cells (i.e., insulin expressing-cells that do not secrete insulin in response to glucose) express lower levels of MafA than mature beta cells, and that in vitro treatment of these immature beta cells with one or more TR pathway agonists promotes conversion of an immature beta cell to a mature beta cell (e.g., beta cell maturation). Accordingly, the present disclosure provides methods and compositions for promoting beta cell maturation in vitro using one or more TR pathway agonists. The present disclosure also provides methods for using mature beta cells generated using the methods disclosed herein in cell therapy methods, for example, in the treatment of conditions in which a reduction in beta cell number or beta cell function is causative or contributory.

Within the healthy adult pancreas reside a heterogeneous population of cells known as islet cells, of which one type is known as insulin expressing beta cells. This population of cells includes mature beta cells, in which insulin secretion can be elicited by increases in plasma glucose; these cells are also referred to as glucose-responsive insulin secreting cells. In addition, the population also includes beta cells that express insulin, but do not secrete insulin in a glucose dependent manner, referred to herein as immature beta cells or glucose insensitive insulin expressing cells. (Grill, Am. J. Physiol., 240:E24-31, 1981; Bliss et al., Am. J. Physiol., 263:E890-896, 1992, 1992; Freinkel et al., Diabetes, 33:1028-1038, 1984; Hellerstrom et al., Diabetes, 40:89-93, 1984). A reduction in the number or function of mature beta cells can promote disease.

Methods are available for producing stem or progenitor derived β cells for use in cell replacement therapy (Kroon et al., Nat. Biotech., 26:443-52, 2008; D'Amour et al., Nat. Biotech., 24:1392-401, 2006; Jiang et al., Stem Cell, 7:333-344, 2007; Baetge, Diabetes, Obesity, and Metabolism, 10:186-194, 2008; U.S. Pat. No. 7,510,876 (and references cited therein)). However, such stem or progenitor derived β cells are typically not glucose responsive (e.g., the methods result in the generation only of immature β cells). Therefore, although the cells express insulin, they do not secrete insulin in response to glucose. This limits the value of these cells in cell therapy (D'Amour et al., supra; Kroon et al., supra; Baetge, supra). Recent data supports that after several weeks as grafts in vivo, these insulin+ cells become glucose responsive and acquire glucose-responsive insulin secretion. (Kroon et. al., supra). Recent data also indicates that MafA and MafA-transcriptional targets are important in insulin biosynthesis (Nishimura et al., Developmental Biology, 293:526-39, 2006; Wang et al., Diabetologia 50:348-58, 2007). Furthermore, it is reported that fetal and neonatal rodent islets do not secrete insulin in response to glucose (Bliss and Sharp, Am. J. Phys., 263:E890-6, 1992).

The importance of MafA in the development of glucose sensitivity is shown herein. Specifically, the data provided herein demonstrates that MafA expression is low in islets at birth and that overexpression of MafA in 1 day old islets promotes glucose-responsive insulin secretion. Consistent with this, a positive correlation exists between the in vivo acquisition of glucose sensitivity in islet cells and the level of MafA. Specifically, the data presented herein show an increase in MafA and its targets between days 7 and 9 in neonatal pancreatic islets. As demonstrated herein, TR pathway agonists can be used to increase MafA expression in immature beta cells and thereby increase glucose sensitivity (e.g., induce beta cell maturity).

The effect of thyroid hormones on pancreatic cells is controversial. For example, one group reports that T3 thyroid hormone promotes cell proliferation and reduces apoptosis in beta cells (Verga et al., J. Cell., Physiol., 206:309-321, 2006). Data from a second group contradicts these findings by showing that T3 promotes increased proliferation in pancreatic acinar cells but not in pancreatic islet (e.g., beta cells) and ductal cells (Ledda-Columbano et al., J. Endocrinol., 185: 393-399, 2005). A third group reported that in vivo administration of T3 thyroid hormone reduced the incidence of type I diabetes and increased beta cell mass in rats (Hartoft-Nielson et al., Autoimmunity, 42:131-138, 2009).

Other groups have focused on the in vivo effects of thyroid hormones on insulin secretion. While several groups report a positive correlation between insulin secretion and plasma T3 thyroid hormone levels in vivo (Ortega et al., Eur. J. Endocrinol., 158:217-221, 2008; Ikeda et al., Biochem. Pharmacol., 40:1769-1771, 1990), other groups suggest that the in vivo association between thyroid hormone and insulin secretion is limited to T4 (Yamamoto et al., Endocrinol Jpn, 34:605-609, 1987; Ikeda et al., Biochem. Pharmacol., 40:1769-1771, 1990). In general, published data tends to teach that in vitro administration of thyroid hormone, and hyperthyroidism, promotes either no change in insulin secretion or a decrease in insulin secretion (Roubsanthisuk et al., J. Med. Assoc. Thai., 89 Suppl. 5:S133-S140, 2006; Lovejoy et al., Metabolism, 46:1424-1428, 1997).

T3 thyroid hormone has also been used to treat the non-insulin expressing human epithelial cell line HPANC-1 (Human pancreatic carcinoma, epithelial-like cell line-1) and has been shown to promote differentiation of the cell line to or towards a glucose responsive insulin secreting cell line (Misiti et al., J. Cell. Physiol., 204:286-296, 2005).

MafA

The Maf family proteins regulate tissue-specific gene expression and cell differentiation in a wide variety of tissues. The basic-leucine zipper transcription factor MafA is a glucose-responsive insulin gene transactivator expressed selectively in pancreatic beta cells, which serves as a late stage beta cell maturation factor (Nishimura et al., supra). MafA regulates insulin expression by binding to the conserved C1/RIPE3b and regulates insulin expression synergistically with Pdx1 and Beta2. MafA−/− mice develop age-related diabetes. In embryonic insulin-producing cells, MafA expression is preceded by MafB expression (Nishimura et al., Dev. Biol., 293:526-539, 2006).

MafA also regulates genes involved in β-cell function such as Glucose transporter 2, Glucagon-like peptide I receptor, and Prohormone convertase 1/3. MafA expression in beta cells is known to be regulated at both the transcriptional and post-translational levels by glucose and oxidative stress. (For a review of MafA see, e.g., Aramata et al., Endocrine journal, 659-666, 2007).

As shown herein, MafA expression is lower in immature beta cells than in mature beta cells and MafA expression can be increased, e.g., in immature beta cells using one or more TR pathways agonists.

In some embodiments, MafA can be used as a marker to distinguish between immature beta cells and mature beta cells. In some embodiments, MafA expression levels can be detected in a first control cell that is known to be an immature beta cell. The MafA level in the first cell can then be compared to the MafA level in a second cell known or suspected to be a mature beta (e.g., a cell contacted with a TR agonist). Second cells that are mature beta cells will exhibit higher MafA expression levels than the MafA expression level in the first cell. For example, MafA expression levels in a second cell that is a mature beta cell can be 10%, 20%, 50%, 100%, 200%, 500%, 800% 900%, 1000% or more higher than the MafA expression level in the first cell (e.g., an immature beta cell).

Exemplary MafA sequences include NCBI Accession No. NM_201589, Ac105118 (human RNA), NP963883 (human). Antibodies suitable for detecting MafA are known in the art, for example, Bethyl laboratories, Montgomery, Tex., Catalog #A300-611A, IHC-00352. In some embodiments, MafA sequences are disclosed in U.S. Pat. No. 7,524,492.

In some embodiments, MafA expression levels can be increased in a MafA expressing cell by contacting the cell with one or more TR pathway agonists. In some embodiments, the present disclosure provides methods for increasing MafA expression in a MafB expressing insulin containing cell. Such methods include obtaining a MafA and/or a MafB expressing cell and contacting the cell with one or more TR pathway agonists. The level of MafA can be assessed directly by detecting the expression level of MafA protein or mRNA. Alternatively, or in addition, the level of MafA can be assessed indirectly by assessing glucose-dependent insulin secretion from the cell, wherein an increase in the level of glucose-dependent insulin secretion from the cell indicates that an increase in the level of MafA has occurred.

Beta Cell Maturation

In some embodiments, the present disclosure provides compositions and methods for promoting the conversion of an immature beta cell to or towards a mature beta cell (e.g., (1) conversion of a target cell from non-glucose responsive insulin expressing cell to a glucose-responsive insulin secreting phenotype; (2) conversion of a target cell from which a first level of insulin is secreted in the presence of a given (e.g., elevated) level glucose to a cell from which a second higher level of insulin is secreted in the presence of the same level of glucose; or (3) conversion of a target cell with a first level of MafA to a cell with a second higher level of MafA) in vitro.

Target Cell Selection—Immature Beta Cells

In some embodiments, target cells suitable for use in the present invention include immature beta cells.

As used herein, the term immature beta cell includes any cell (or population of cells) that can express insulin (e.g., insulin mRNA and/or protein) or that contains insulin, but that does not secrete insulin in response to changes in glucose)); and/or any cell that can secrete insulin in response to glucose at a first level, where the first level is lower than the level desired or required or lower than the level of insulin secretion from a mature healthy glucose-responsive insulin expressing beta cell/islet (e.g., in a healthy subject); or a cell that constitutively secretes insulin, e.g., at a low level, but does not alter secretion levels or rates in response to changes in ambient glucose concentrations. Immature beta cells thus have some characteristics of mature beta cells (i.e., they express insulin (e.g., mRNA and/or protein) but do not secrete insulin in response to changes in glucose stimulation).

In some embodiments, immature beta cells can be immature beta cells derived from (i.e., obtained by differentiating) stem and/or progenitor cells such as hepatocytes (e.g., trans-differentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells) (see e.g., Sipione et al., Diabetologia, 47:499-508, 2004), and others known in the art. In some embodiments, stem or progenitor cells can include cells that will differentiate into immature beta cells spontaneously or upon induction.

Methods for differentiating such cells to or towards immature beta cells are know in the art (see, e.g., Kroon et al., Nat. Biotech., 26:443-52, 2008; D'Amour et al., Nat. Biotech., 24:1392-401, 2006; Jiang et al., Stem Cell, '7:333-344, 2007; Eshpeter et al., Cell Prolif. 41, 843-858 (2008); Maehr et al., Proc Natl Acad Sci USA. 2009; 106:15768-73; Xu et al., Cloning Stem Cells. 2006 8:96-107; Zhang et al., Cell Res. 2009 19:429-38; Tateishi et al., J Biol. Chem. 2008; 283: 31601-7; Baetge, Diabetes, Obesity, and Metabolism, 10:186-194, 2008; Cai et al., Journal of Molecular Cell Biology 2:50-60 (2010); and U.S. Pat. No. 7,510,876 (and references cited therein)). See also Van Hoof et al., Stem Cell Res. 2009 September-November; 3(2-3):73-87.

In some embodiments, the cell is a primary cell or is derived directly from (e.g., within 2 generations of) a primary cell. In some embodiments, the cell is an isolated primary immature beta cell.

In some embodiments, an immature beta cell does not include a HPANC-1 (Human pancreatic carcinoma, epithelial-like cell line-1) cell. In some embodiments, an immature beta cell includes a HPANC-1 cell that has been differentiated to a cell with characteristics of a beta cell (e.g., the cell expresses insulin (e.g., mRNA and protein) prior to treatment using the methods described herein (e.g., prior to treatment with a TR pathway agonist)).

In some embodiments, the term immature beta cell includes a substantially pure population of immature beta cells, where 50%, 60%, 70%, 80%, 90%, 95%, 98%, 99%, and 100% of the cells in the population are immature beta cells. Methods for identifying immature beta cells are described herein. However, the starting population need not be purified, and a homogeneous population of cells, e.g., in which only 10%-20% or more of the cells are immature beta cells, can also be used. In either case, if desired the mature beta cells can be purified from the non-beta cells after the maturation process is complete.

In some embodiments, immature beta cells express insulin (e.g., at a level lower than (e.g., have mRNA levels of up to 5%, 10%, 15%, 20%, 25%, 30%, 40%, or 50% of) the level of insulin in a healthy adult beta cell) or insulin plus at least one of (1)-(5): (1) MafB; (2) MafB and MafA; (3) higher levels of MafB than MafA; (4) MafA at a level lower than (e.g., have mRNA levels of up to 5%, 10%, 15%, 20%, 25%, 30%, 40%, or 50% of) the level of MafA in a healthy adult beta cell (e.g., a mature glucose-responsive insulin secreting beta cell); and/or (5) one or more, two or more, three or more, or all four of MMP2 (human sequence in GenBank at Acc. Nos. NM_001127891.1 (nucleic acid, isoform b), NP_001121363.1 (protein, isoform b) NM_004530.4 (nucleic acid, isoform a) and NP_004521.1 (protein, isoform a); CK19 (human sequence in GenBank at Acc. Nos.

NM_002276.4 (nucleic acid) and NP_002267.2 (protein); SPD (human sequence in GenBank at Acc. Nos. NM_003019.4 (nucleic acid) and NP_003010.4 (protein); and Frizzled 2 (human sequence in GenBank at Acc. Nos. NM_001466.2 (nucleic acid) and NP_001457.1 (protein). Expression levels can be determined using methods known in the art, e.g., quantitative real-time PCR.

Mature beta cells include any glucose responsive insulin secreting cell (or population of cells), e.g., any cell that can secrete insulin in response to glucose at the same or substantially the same level as a normal healthy (human) glucose-responsive beta cell, and/or a healthy glucose responsive beta cell/islet. Methods for identifying mature beta cells are known in the art and are described herein. In some embodiments, mature beta cells express insulin and MafA plus one or more of NeuroD (human sequences in GenBank—nucleic acid: NM_002500.2; amino acid: NP_002491.2), NK6 homeobox 1 (NKX6.1) (human sequences in GenBank—nucleic acid: NM_006168.2; amino acid: NP_006159.2), and pancreatic and duodenal homeobox 1 (PDX1) (human sequences in GenBank—nucleic acid: NM_000209.3; amino acid: NP_000200.1).

For the purpose of comparing insulin and MafA message/protein in stem/progenitor/iPS derived insulin producing cells, adult human beta cells/islets can be prepared using known methods (see, e.g., Linetsky et al., Diabetes 46:1120-1123 (1997)) from a non-diabetic (HbA1c of 6 or lower) cadaver or organ donor between the ages of 18 and 50, with cold ischemia of less than 8 hours, and with an islet purity of greater than 80%. Total RNA isolated from these islets can then be reverse transcribed into cDNA and used to quantify insulin and MafA message using real time RT-PCR. The amount of insulin and MafA message from these adult islets can be used as reference (e.g., 100%) to determine the relative amount of insulin and MafA in a preparation of immature beta cells determined using the same or comparable methods.

Insulin protein content of adult islets can also be determined using methods known in the art, e.g., using the following exemplary protocol. Islets are sonicated in acid ethanol and stored overnight at 4° C. The next day, homogenate is centrifuged (2,500 rpm for 10 minutes); the supernatant can be stored at −20° C. until used. Insulin concentration in the supernatant is measured, e.g., by radioimmunoassay OR ELISA, e.g., using commercially available kits (e.g., from Linco Research). Total protein content of the extract can be measured by the bicinchoninic acid protein assay kit (Pierce, Rockford, Ill.) using BSA as standard. These values can then be used as references (e.g., 100% referenced) to determine the relative insulin and MafA protein in a preparation of immature beta cells determined using the same or comparable methods.

Maturation Treatments

In some embodiments, the methods include obtaining an immature beta cell or a population of immature beta cells (e.g., a substantially pure population of immature beta cells) and contacting the cell or cells with one or more thyroid receptor (TR) pathway agonists (e.g., T3) under conditions and for a time suitable for the cell to become a mature beta cell. As used herein, the term TR pathway agonist refers to any agent that can increase the activity of a TR (e.g., TR $\alpha$1, $\alpha$2, and/or beta), such as, e.g., TR ligands, downstream targets of TR, and/or agents that mimic the activity of a TR and/or a TR hormone.

In some embodiments, the immature beta cell or population of immature beta cells is contacted with one or more TR pathway agonists (e.g., T3) at a concentration of between $10^{-1}$-$10^{-20}$ M (e.g., $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, $10^{-16}$, $10^{-17}$, $10^{-18}$, $10^{-19}$, $10^{-20}$ M and more). In some embodiments, the concentration of T3 is $10^{-11}$. In some embodiments, the immature beta cell or population of immature beta cells are contacted with one or more TR pathway agonists (e.g., T3) in charcoal-stripped fetal bovine serum (CS-FBS (e.g., available from GIBCO). In some embodiments, the immature beta cell or population of immature beta cells are contacted with the TR pathway agonist for 1-10 days (e.g., 1, 2, 3, 4, 5, 6, 7, 8, 9, 10, or more days). In some embodiments, the immature beta cell or population of immature beta cells are contacted with the TR pathway agonist for 5 days.

In some embodiments, one or more TR pathway agonists can be administered in vivo to a subject in need thereof. Exemplary subjects include premature infants and subjects receiving implants of mature beta cells.

Thyroid Hormone Receptor Pathway Agonists

In some embodiments, the TR pathway agonist includes one or more of, for example, TR $\alpha$1 (e.g., National Center for Biotechnology Information (NCBI) Accession No. NM_003250), TR$\alpha$2 (e.g., NCBI Accession No. NM_199334), TRbeta (e.g., NCBI Accession No. NM_00461, NM_001128176, and NM_00112877), T3 thyroid hormone (e.g., triiodothyronine or L-3,5,3'-triiodothyronine), T4 thyroid hormone (e.g., thyroxine or L-3,5,3',5'-tetraiodothyronine), selective and non-selective thyromimetics, TRB selective agonist-GC-1, GC-24, 4-Hydroxy-PCB 106, MB07811, MB07344.

In some embodiments, the TR pathway agonist is a thyroid hormone analogue. A number of thyroid hormone analogs are known in the art (see e.g., U.S. Publication No. 2008/0221210; Ocasio and Scanlan, ACS Chem. Biol., 1:585-593, 2006; U.S. Pat. No. 6,951,844), for example, 3,5-diiodothyropropionic acid (DITPA); the selective TR-beta agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), and 3,5-diiodothyropropionic acid (DITPA). See, e.g., Josseaume and Lorcy, Ann Endocrinol (Paris). 2008 September; 69 Suppl 1:S33-6; Trost et al., Endocrinology. 2000; 141:3057-3064; Grover et al., Endocrinology. 2004; 145; 1656-1661; Villicev et al., J Endocrinol. 2007; 193:21-29; Ribeiro, Thyroid. 2008; 18:197-203; Moreno et al., Thyroid. 2008 February; 18(2): 239-53; Horrum et al., Biochem Mol Biol Int (1996) 38: 61-72; Cleamond et al., J. Med. Chem., 1970, 13 (2), pp 215-220; Underwood et al. Nature, Vol. 324: pp. 425-429 (1986); Grover et. al. PNAS, Vol. 100: pp. 10067-10072 (2003); Grover, Endocrinology, Vol. 145: pp. 1656-1661 (2004); Li et. al. PCT Int. Appl. WO 9900353 (1999); Scanlan et al., PCT Int. Appl. WO 9857919 (1998); Keith A. Walker et. al. U.S. Pat. No. 5,284,971 (1994); Erion et. al. PCT Int. Appl. WO 2005051298 (2005); Johan, Current Pharmaceutical Design, Vol. 10(28): pp. 3525-3532 (2004); Expert Opin. Ther. Patents, Vol. 14: pp. 1169-1183 (2004); Scalan, Current Opinion in Drug Discovery & Development, Vol. 4 (5): pp. 614-622 (2001); and Webb, Expert Opinion on Investigational Drugs, Vol. 13 (5): pp. 489-500 (2004). See also USPTO PG Pub 20090022806 (describing nanoparticle and polymer formulations for thyroid hormone analogs and formulations and uses thereof) and PG Pub 20090082310 (describing prodrugs of thyroid hormone analogs, e.g., pyridazinone analogs).

In some embodiments, the thyroid receptor agonist is specific for one or both of THR isoform alpha1 or beta1.

In some embodiments, levels of endogenous thyroid receptor agonists are increased by modulating activity of a deiodinase, e.g., DI02 or DI03. See, e.g., Kohrle et al., Mol Cell Endocrinol. 1999 May 25; 151(1-2):103-19.

In some embodiments, TR pathway agonists can be formulated according to their intended method of use. Formulation methods are known in the art, see, e.g., the books in the series *Drugs and the Pharmaceutical Sciences: a Series of Textbooks and Monographs* (Dekker, NY).

Examination of Beta Cell Maturity

In some embodiments, beta cell maturity can be assessed following treatment of a immature beta cell with a TR agonist, e.g., by detecting an increase in the level of glucose-dependent insulin secretion from the cell. For example, in some embodiments, a first level of insulin secretion can be detected before treatment of the cell and subsequent levels of insulin secretion can be detected during and/or following treatment of the cell, e.g., following exposure of the cells to glucose. The subsequent levels of insulin secretion can then be compared to the first level of insulin. In some embodiments, a mature beta cell can be identified by detecting a higher level of insulin secretion from the cell than the first level of insulin secretion (e.g., a level of insulin secretion that is 10, 20, 30, 40, 50, 60, 70, 80, 90, 100, 200, 300, 500, 800, 1000, 2000%, and above, higher than the first level of insulin).

In some embodiments, beta cell maturity can be assessed following treatment of a immature beta cell with a TR agonist, e.g., by detecting an increase in the level of MafA expression in the cell, e.g., following exposure of the cells to glucose. For example, in some embodiments, a first level of MafA can be detected before treatment of the cell and subsequent levels of MafA can be detected during and/or following treatment of the cell, e.g., following exposure of the cells to glucose. The subsequent levels of MafA can then be compared to the first level of MafA. In some embodiments, a mature beta cell can be identified by detecting a higher level of MafA in the cell than the first level of MafA (e.g., a level of MafA that is 10%, 20%, 50%, 100%, 200%, 500%, 800% 900%, 1000% or more higher than the first level of MafA).

Where a population of cells is used, glucose-stimulated insulin secretion or MafA expressions can be assessed in a subset of the cells.

In some embodiments, insulin secretion can be assessed by measuring the level (e.g., concentration) of insulin in the cell culture medium following treatment of the cells and following exposure of the cells to glucose. Methods for detecting and quantifying insulin levels are know in the art. For example, such methods include immunohistochemical detection, ELISA, and reverse hemolytic plaque assays, e.g., as shown in Example 3.

In some embodiments, beta cell maturity can be assessed microscopically.

To purify beta cells from non-beta cells (e.g., to obtain a substantially purified population of beta cells) one can use Newport green followed by known fluorescence-activated cell sorting (FACS) (see, e.g., Parnaud, Diabetologia (2008) 51:91-100); auto-fluorescence in human beta cells has also been reported (Lorella Marselli, J Clin Endocrinol Metab. March 2008, 93(3):1046-1053) and that can be used to sort them out from a mixture of cells. Since it is expected that T3 treatment will convert most if not all beta cells into mature beta cells, purification using this method on a population of cells that has been treated with T3 is expected to yield a substantially pure population of mature beta cells. In some embodiments, a more highly purified population can be obtained using measurements of glucose levels or metabolism (it is expected that mature beta cells may metabolize more glucose), or measurement of amounts of intercellular $Ca^{2+}$ or metabolites like NADPH (it is expected that mature beta cells may have higher amounts). These parameters can optionally be used to separate cells using FACS based approaches.

Effective Dose

Toxicity and therapeutic efficacy of the compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Methods of Treatment

In some embodiments, the mature beta cells generated using the methods disclosed herein can be used to treat diabetes and other conditions in which a reduction in beta cell number or beta cell function is causative or contributory in a subject.

Subject Selection

In some embodiments, cells contacted with one or more TR pathway agonists can be used for treating subjects who have, or who are at risk for developing, diabetes or a diabetes disorder. In some embodiments, the term "diabetes" as used herein includes, but is not limited to type 1 diabetes, type 2 diabetes, gestational diabetes, neonatal diabetes, mitochondrial diabetes, impaired fasting glucose, impaired glucose tolerance, or diabetes caused by surgery, medications, infections, pancreatic disease, genetic abnormality, and/or other illnesses.

In some embodiments, a subject who has, or is at risk for developing, diabetes or a diabetes disorder can be identified by their physician or can have been previously diagnosed by their physician. In some embodiments, a subject who has, or is at risk for developing diabetes can be identified by a health-care provider based on, e.g., a physical exam, the presence or absence of symptoms associated with diabetes (e.g., excessive thirst or hunger, exhaustion or fatigue, frequent urination, loss or gain of weight, blurry vision, and the presence of slow healing cuts or sores), medical history, and/or based on the results of specific glucose tests (e.g., the oral glucose tolerance test and/or fasting blood glucose level test (a value above 126 mg/dl on at least two occasions typically means a person has diabetes. Normal people have fasting sugar levels that generally run between 70-100 mg/dl)).

Cell Therapy

Cell therapy methods can be used to promote increased glucose-dependent insulin expression, activity, or secretion in or from a cell capable of insulin expression or secretion. In some embodiments, cells contacted with one or more TR pathway agonists can be transplanted or implanted into a subject in need of such treatment. The cell culture methods required to practice these methods, including methods for identifying and selecting suitable cell types and implantation methods are known in the art and are described below. Methods for determining how many cells to implant into a subject and where to implant the cells within the subject can be determined by a skilled practitioner. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used.

In some embodiments, treatment of a subject can include administration of cell therapy comprising mature or immature beta cells, and co-administration, e.g. local to the site of cell transplant, of one or more TR pathway agonists (e.g., T3 and/or T4).

EXAMPLES

The invention is further described in the following examples, which do not limit the scope of the invention described in the claims.

Example 1

Age is an Important Determinant for Functional Heterogeneity in Beta Cells

Markers that can be used to track the differentiation of a stem cell or progenitor cell to or towards a mature beta cell would be useful.

Using gene profiling (Affymetrix microarrays) of laser capture microdissected beta cell cores from new and mature islets of the same pancreas, 87 genes/ESTs were observed to be more highly expressed in newly regenerated islets than in mature islets from both the same animals and sham animals.

Differential expression of 7 cell surface molecule genes and cytokeratin 19 (CK 19) was confirmed by quantitative real-time PCR. Total RNA was isolated using the picoRNA extraction kit (Arcturus) and reverse transcribed to obtain cDNA using SuperScript reverse transcriptase (Invitrogen). Real-time quantitative (q) PCR with SYBR green detection was performed using specific primers (see Aye et al., Journal of Histochemistry & Cytochemistry 58(4): 369-376 (2010). Samples were normalized to a control gene (S25), and the comparative CT (threshold cycle) method used to calculate gene expression levels. Of these, CD24, MMP-2, surfactant protein-D (SPD) and CK 19 protein were expressed selectively in beta cells of new islets with little to no expression in mature islets from the same pancreas as shown by immunostaining See Aye et al., (2010) supra.

Over a third of the enhanced genes/ESTs in new islets were highly expressed in pancreatic ducts but not in adult islets. Such markers provide tools for determining the state of differentiation of ductal progenitor or progenitor cell-derived beta cells, much as in hematopoietic development.

To test the generality of these markers of newly formed beta cells, as well as several identified more recently (frizzled 2, MMP14), their expression was analyzed during the perinatal period, a time of recognized beta cell immaturity. As shown in FIG. 1, from embryonic days 18 and 20, birth, 24 h, 48 h, 72 h, 7 days and adulthood, MMP2, CK19, SPD and Frizzled 2 are true markers of new and immature beta cells. Parallel gene profiling experiments of LCM captured beta cell cores of P1 neonatal islets were also performed for comparison with the adult beta cells to evaluate their similarities and differences.

Figure 2A:
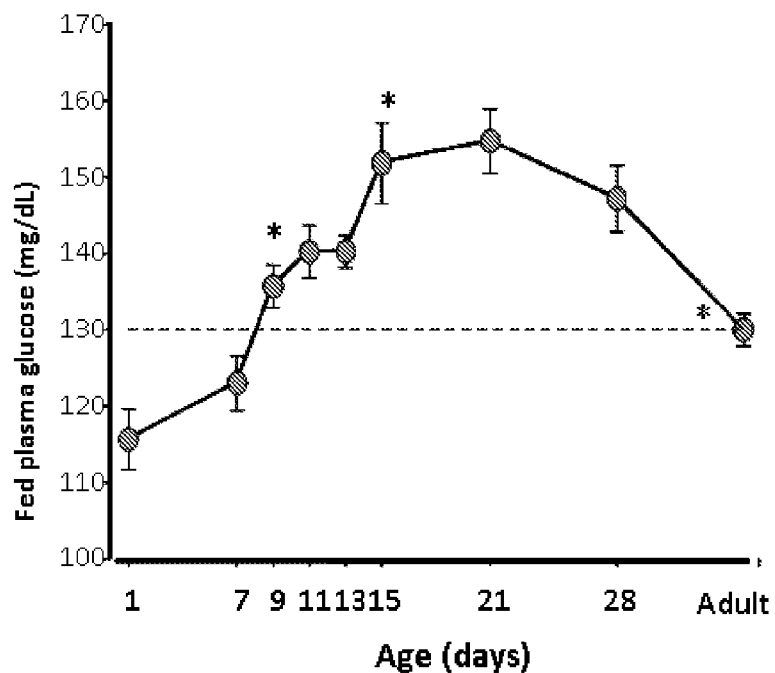
FIGS. 2A-2C are line graphs showing plasma fed glucose (A), insulin (B), and T4 thyroid hormone (C) levels in rats of varying ages.
Figure 2B:
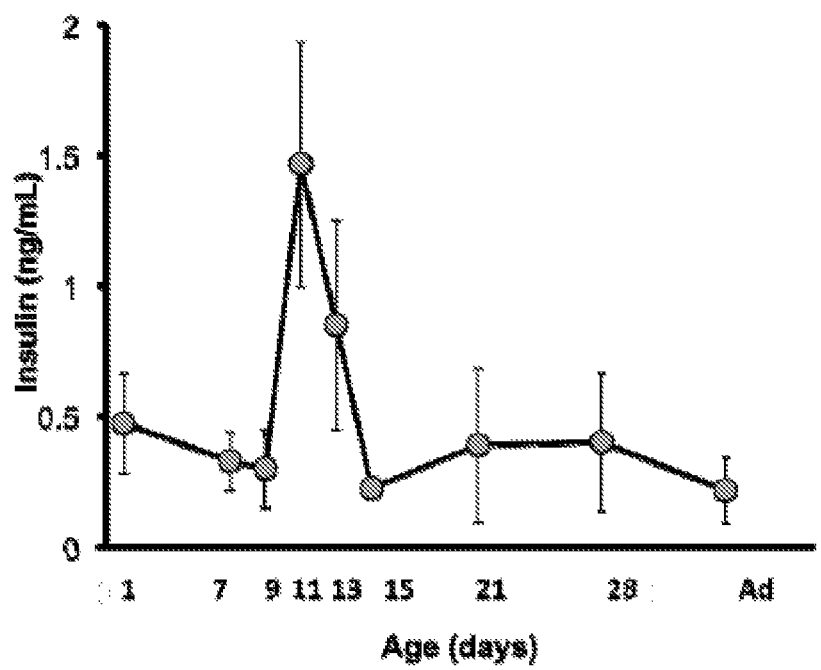
Figure 2C:
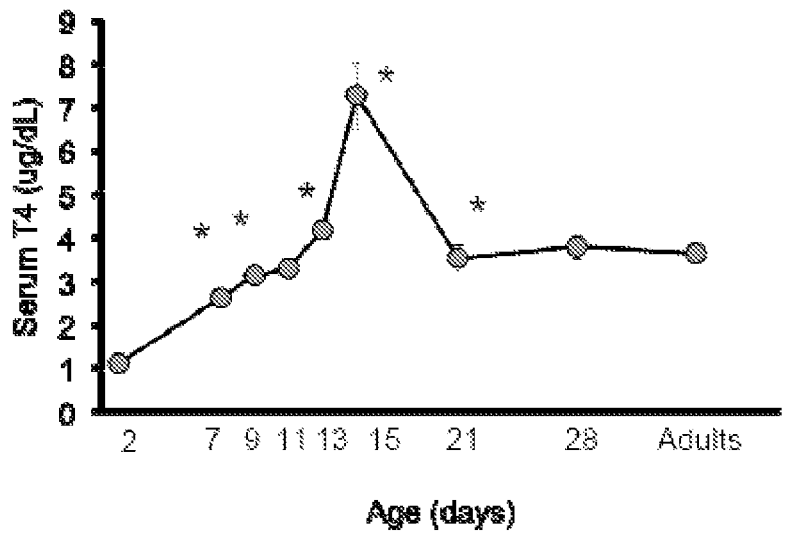

As shown in FIG. 2A, blood glucose levels peaked at P15-21 and started falling by P28. This rise is consistent with the change in diet (eating chow starts about P14-15) and in milk composition, which increases in carbohydrate content throughout the nursing period. As shown in FIG. 2B, plasma insulin has a small change around P12. Since thyroid hormone has physiological changes during this period, T4 radioimmunoassay were performed on plasma from rats ranging from P1 to P28. As shown in FIG. 2C, T4 levels at P1 were lower than adult with a progressive increase, which peaked at P15, and attained adult levels by P21.

The observations in FIGS. 2A-C suggest that the adult milieu to which the newly regenerated beta cells are exposed differs markedly from that of the early neonate. Neonatal beta cells have a 7-15 day lag before being exposed to increasing levels of blood glucose, thyroid hormones, corticosterone and prolactin.

One finding from the gene profiling of the P1 neonatal beta cells was that there was a generalized immaturity of the metabolic pathway normally found in beta cells. Using dChip software for analysis, 215 genes/ESTs were observed to be significantly higher and 375 observed to be significantly lower in beta cell-enriched cores of neonatal than adult islets (2 fold differences, $p<0.05$). Among the lower genes were key metabolic genes including the specialized mitochondrial shuttles (malate dehydrogenase, glycerol phosphate dehydrogenase, aspartate aminotransferase, malic enzyme), pyruvate carboxylase and carnitine palmitoyl transferase (CPT) II. As shown in FIG. 3B, differential expression of these enzymes was confirmed by quantitative PCR on RNA from isolated neonatal and adult islets (using $\Delta$CT analysis: 3-13 fold lower in neonatal, $p<0.01$).

By 7 days of age, there were modest increases in most of these genes, which were still expressed at less than 40% of the adult levels. It had been recognized for many years that fetal and neonatal beta cells lack glucose-responsive insulin secretion; glucose responsiveness is established gradually until after weaning (Grill et al., supra; Bliss et al., supra). While single genes have been proposed for this "impaired" or immature secretion (Rorsman et al., Proc. Natl. Acad. Sci. USA., 86:4505-4509, 1989; Tan et al., Diabetes, 51:2989-2996, 2002), the lack of glucose responsiveness in neonatal islets may be due to a generalized or global immaturity of the metabolic specialization of pancreatic beta cells rather than a specific defect.

Figure 3A:
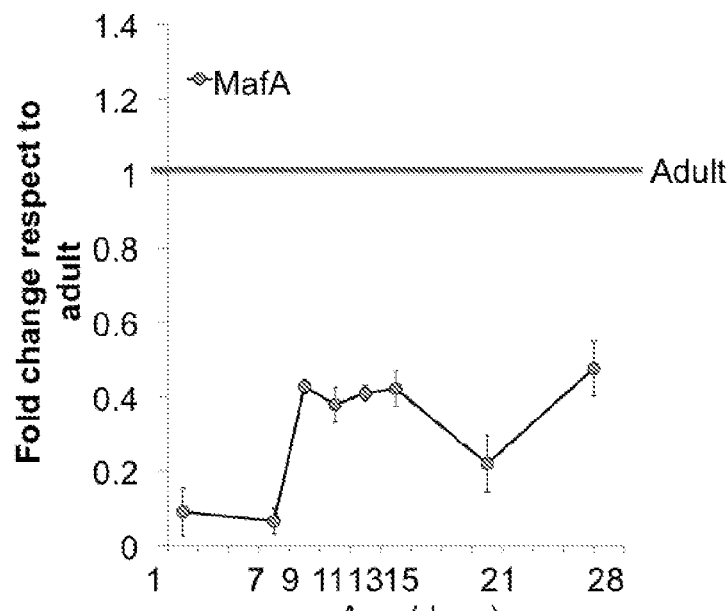
FIG. 3A is a line graph showing MafA expression as assessed using real time PCR during postnatal life and in adult. Data is shown up to P28 normalized in relation to adult islets. Western blot shows that the MafA protein has parallel expression to the mRNA with P1 and P11 have almost undetectable levels compared to adult (Ad) and Min6 cell line.
Figure 3B:
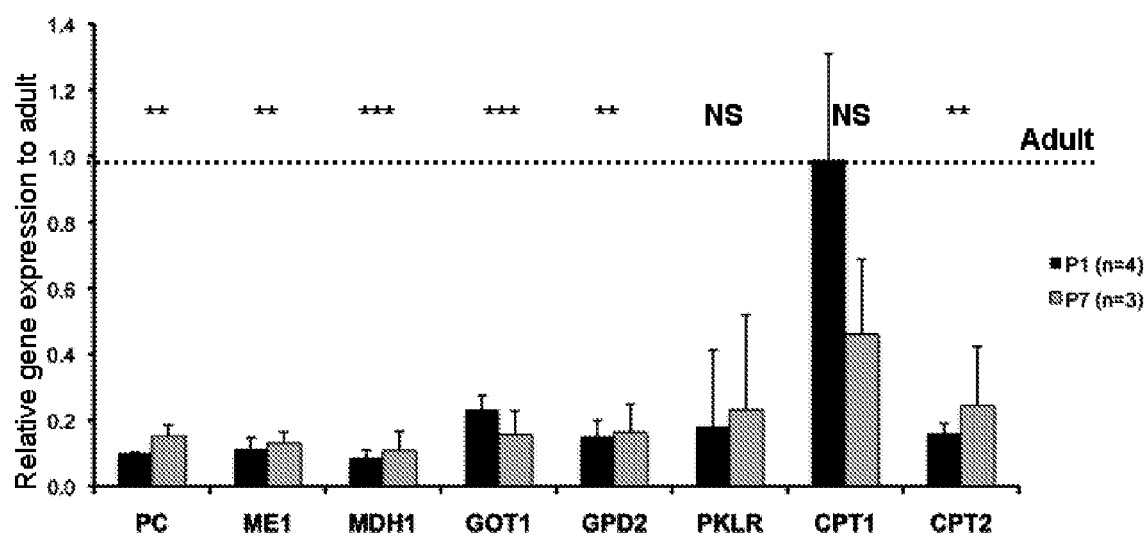
FIG. 3B is a histogram showing gene expression levels in P1 and P7 neonates versus adult rats.
Figure 3C:
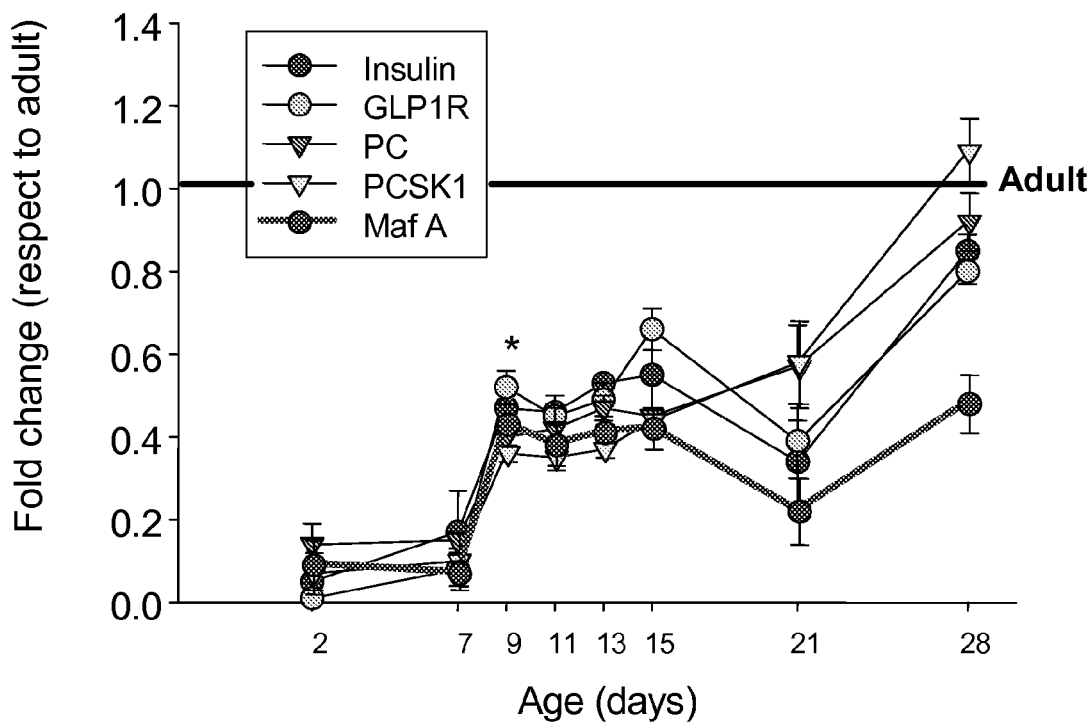
FIG. 3C is a line graph showing the expression levels of MafA and its targets glucagon-like peptide 1 receptor (Glp1R), pyruvate carboxylase, proconvertase 1/3 and insulin in P1 and P7 animals versus adult animals. Each data point represents up to five samples of pooled islets.
Figure 3D:
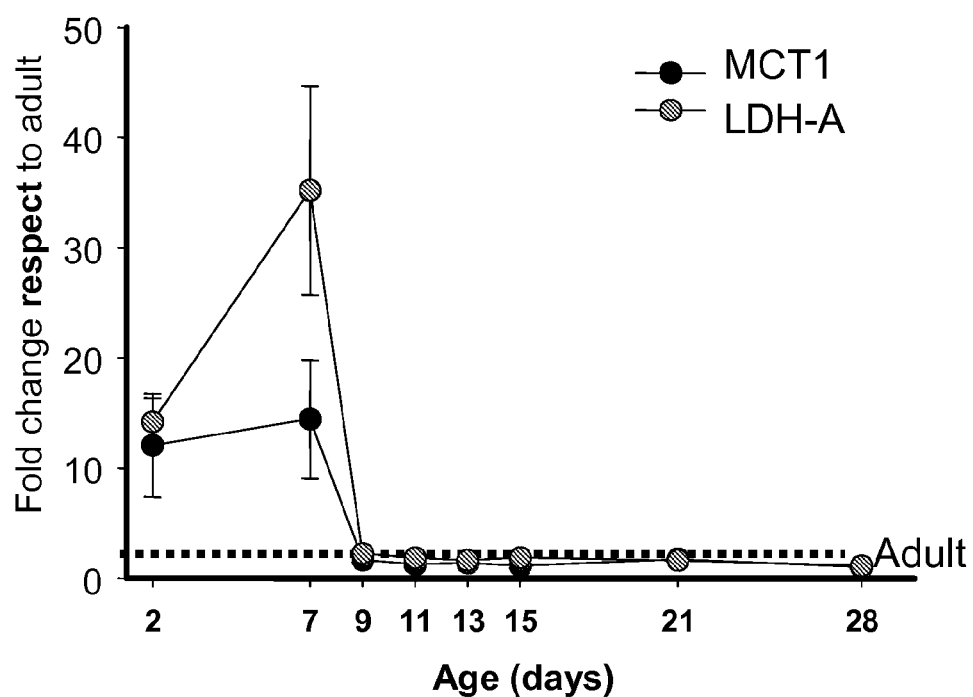
FIGS. 3D-F are line graphs showing expression of genes in animals from birth to one month. qPCR on 4-5 samples each.
Figure 3E:
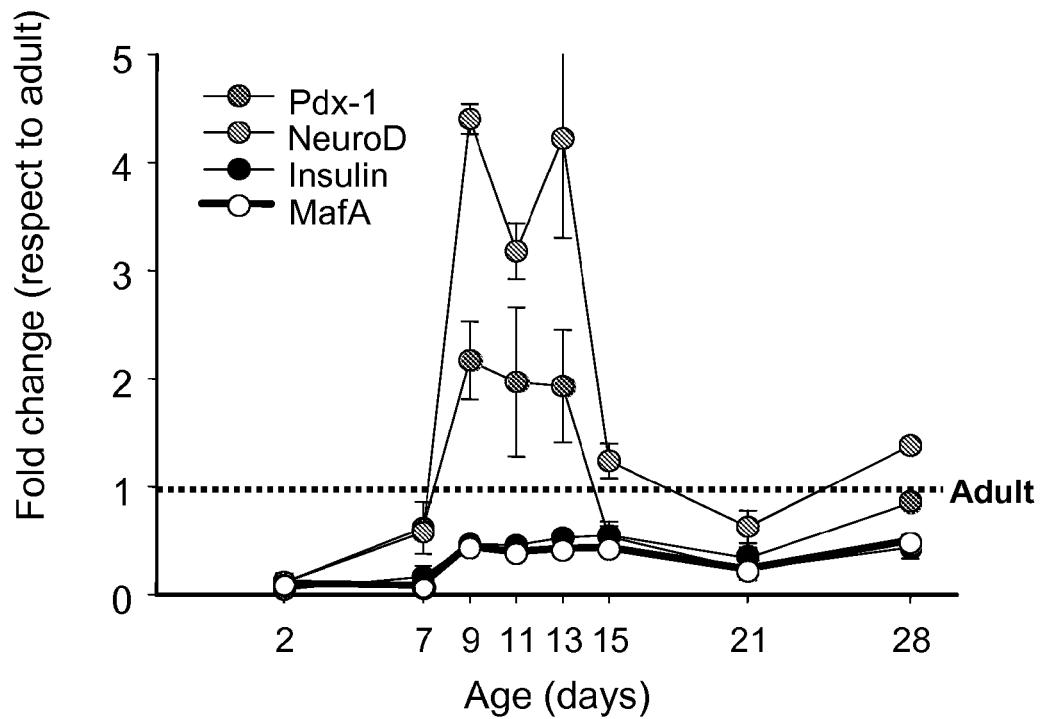
Figure 3F:
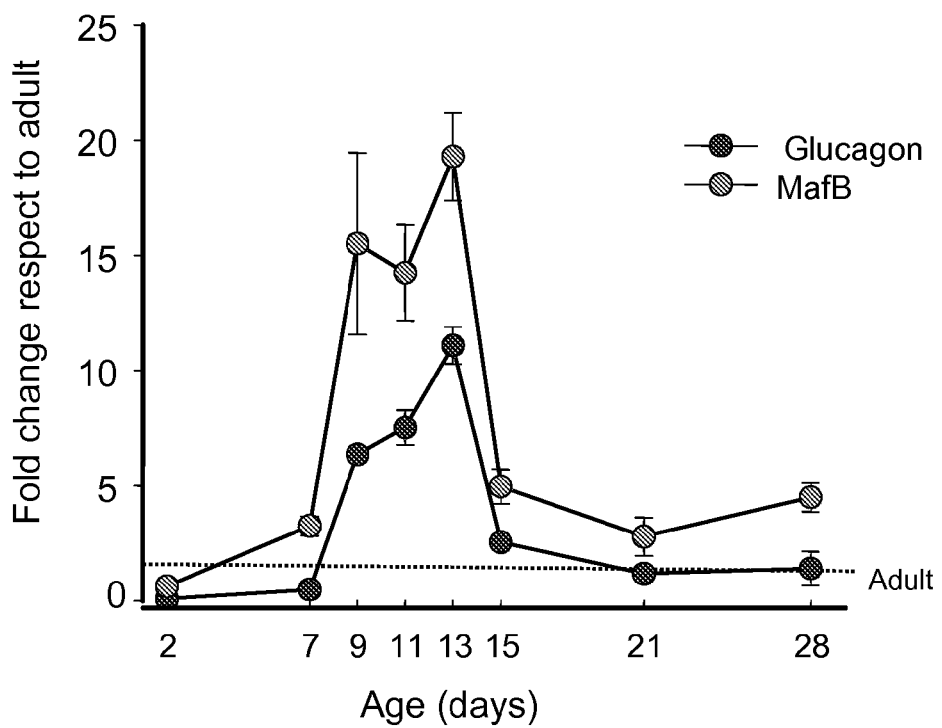

As shown in FIGS. 3D-F, through the neonatal period there are at least three patterns of gene expression in islets that have inflection points at P7-P9 and around P15. As shown in FIG. 3D, LDHA and Monocarboxylate transporter 1 (MCT1) are repressed by P9. FIG. 3E shows that expression of PDX1 and neuroD1 sharply increase at P9 but drop at P15; insulin follows the pattern of MafA. As can be seen in FIG. 3F, both glucagon and MafB have a similar pattern to that of the genes shown in FIG. 3E.

Example 2

MafA and Beta Cell Maturation

MafA is an important late stage beta cell maturation factor (Nishimura et al., supra; Wang et al., Diabetologia, 50:348-358, 2007). The role of MafA in the maturation of neonatal beta cells was analyzed.

As shown in FIG. 3A, MafA is expressed at very low levels during days P1 to P28 compared to adult. As shown in FIG. 3C, in neonatal (P1, P7) rat islets MafA and a number of its target genes were expressed at very low levels (i.e., 5-20% of adult) and during the first postnatal month (P1, 7, 9, 11, 13, 15, 21 and 28) expression of MafA and its target genes increased. Furthermore, MafA expression at P7 was 9% that of adult, however, by P9 the level of MafA was 43% of adult. Similarly, as shown in FIG. 3C, MafA target genes had significantly increased expression from P7 to P9 and reached near adult levels by P28: insulin increased from 17% to 47%, GLP1R from 8% to 52%, PC from 15% to 40%, and PCSK1 10% to 36%. These data strongly support that MafA expression levels are reduced in immature neonatal beta cells. These data also suggest that reduced expression/activity of MafA in neonatal islets contributes to the immaturity of neonatal beta cells and that maturation of immature insulin-producing cells continues through the neonatal period.

Figure 4A:
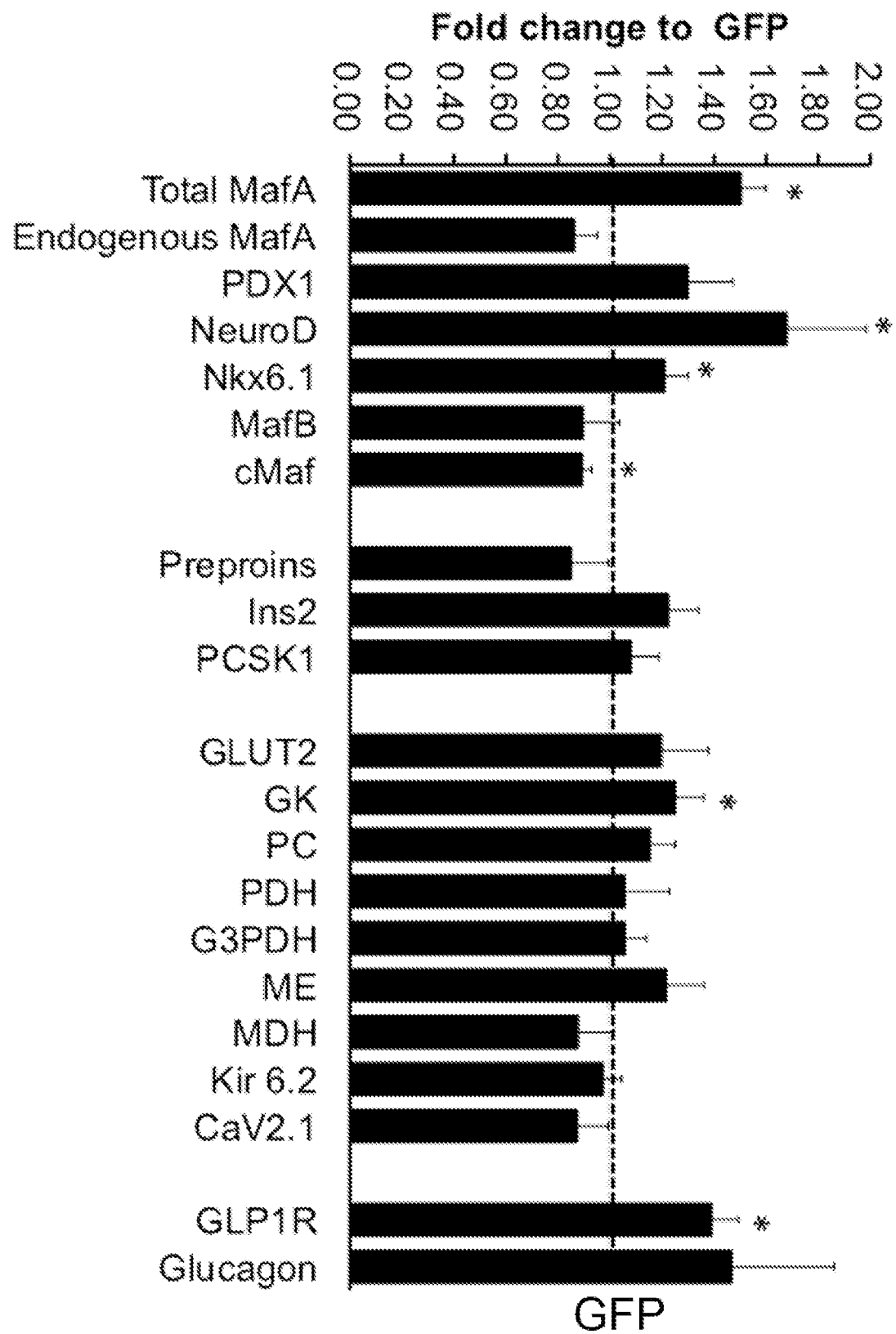
FIG. 4A is a histogram showing the expression levels of MafA and a number of genes important for β cell function in P2 islet cells overexpressing adenoviral MafA. After MafA overexpression, some genes thought to be important for the β cell phenotype (neurogenic differentiation 1 (NeuroD), NK6 homeobox 1 (NKX6.1), glucokinase and Glp1R) have increased expression compared to infection with Adv-GFP (=1, dotted line). Mean±SEM, n=4-6 independent experiments; *p<0.05.

The functional importance of MafA in the maturation of the neonatal beta cell phenotype was shown using overexpression studies. Briefly, islets were dispersed, plated on gelatin-coated dishes, and around 50% the cells were infected with adenovirus. As shown in FIG. 4A, infection with Adv-MafA in P2 islet cells achieved a significant increase in MafA mRNA level compared to control GFP infected cells (GFP=1, dotted line. After MafA overexpression, some genes thought to be important for the β cell phenotype (NeuroD, Nkx6.1, glucokinase and Glp1R) have increased expression compared to infection with Adv-GFP. Thus over-expression of MafA resulted in increasing levels of mRNA of its target genes to levels similar to those observed in fresh adult islets.

To assess whether MafA overexpression had a functional impact upon insulin secretion, a reverse hemolytic plaque assay (RHPA) was used 4 days post culture. RHPA allows the evaluation of secretion from single beta cells (see, e.g., Bosco et al., Am. J. Physiol., 268:C611-C618, 1995; Aguayo-Mazzucato et al., PLoS ONE, 1:e35, 2006). Briefly, insulin secreted during incubation with glucose binds to anti-insulin antibody and complement and lyses RBCs forming hemolytic immunoplaques around secreting cells. Accordingly, the area of the hemolytic plaque is proportional to the amount of insulin secreted by that individual cell. Glucose-stimulated insulin secretion (GSIS) is reflected by the secretion index: the product of the percentage of secreting cells and the mean area of immunoplaques. RHPA is a very sensitive assay in which the proportion of cells secreting and the robustness of their secretion can be measured. However it is laborious, therefore classic static insulin secretion studies were also performed with an insulin ELISA for measurement. Insulin secretion was measured in static conditions by sequential incubation in 2.6 mM and 16.8 mM glucose in Krebs-Ringer bicarbonate buffer (KRB, 16 mM HEPES and 0.1% BSA, pH 7.4) as previously described (Schuppin et al., In Vitro Cell Dev Biol Anim 29A:339-344 (1993); Salomon et al., Exp Cell Res 162:507-520 (1986)). Supernatants and cells were frozen until assayed for Insulin content.

Figure 4B:
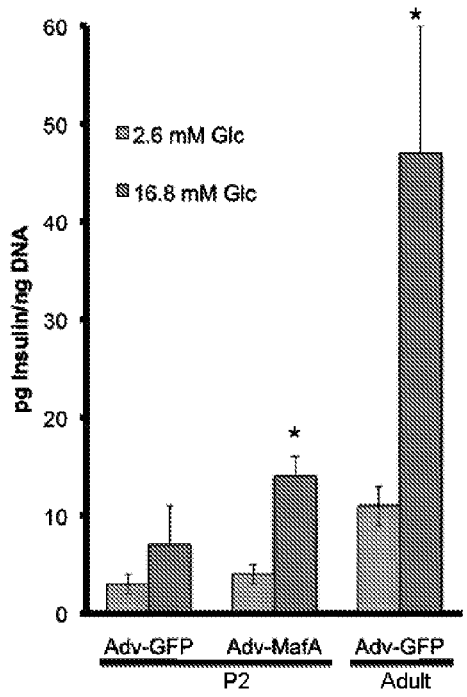
FIG. 4B is a histogram showing glucose-stimulated insulin secretion as assessed by static incubation in P2 and adult β-cells overexpressing adenoviral green fluorescent protein (Ad-GFP) or MafA (Ad-MafA) that were cultured in the presence of 2.6 mM (light bars) or 16.8 mM glucose (dark bars). N=4.
Figure 4C:
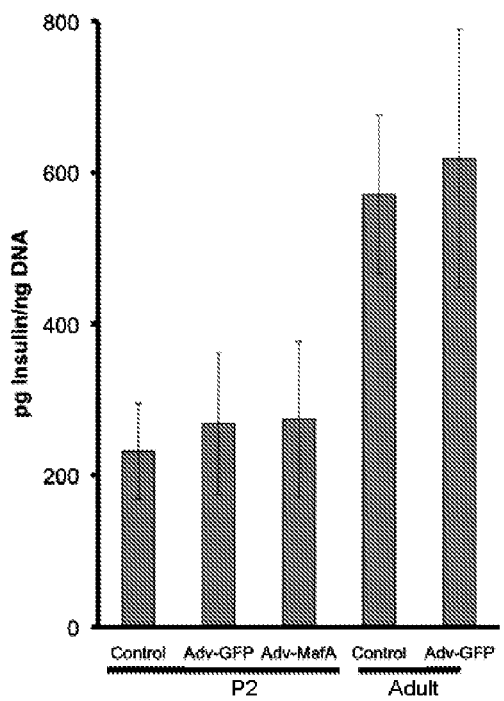
FIG. 4C is a histogram showing the insulin content in the cells tested for secretion in 4B. There was no change in insulin content coinciding with the increase in glucose responsiveness after overexpression of MafA.
Figure 4D:
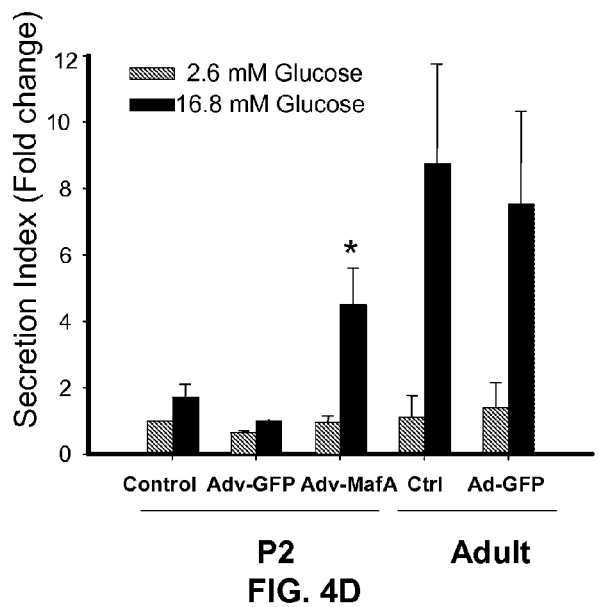
FIGS. 4D-E are a pair of histograms showing (4D) the insulin secretion index (% secreting cells×the plaque area) as assessed by reverse hemolytic plaque assay (RHPA) and (4E) percent secreting cell in P2 and adult β-cells overexpressing adenoviral green fluorescent protein (Ad-GFP) or MafA (Ad-MafA) that were cultured in the presence of 2.6 mM 1 (light bars) or 16.8 mM (dark bars) glucose.
Figure 4E:
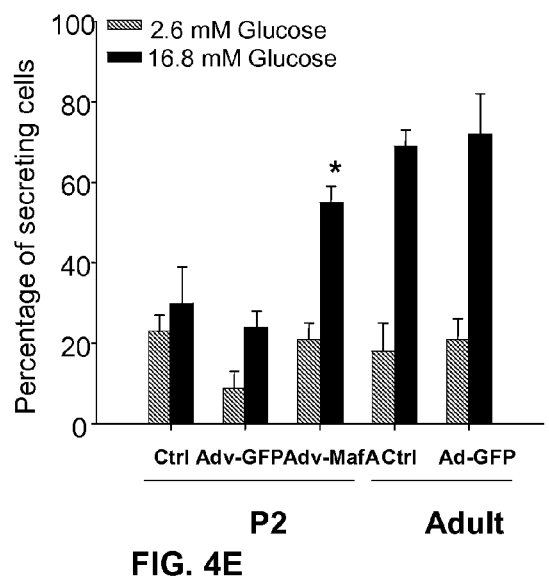
Figure 4F:
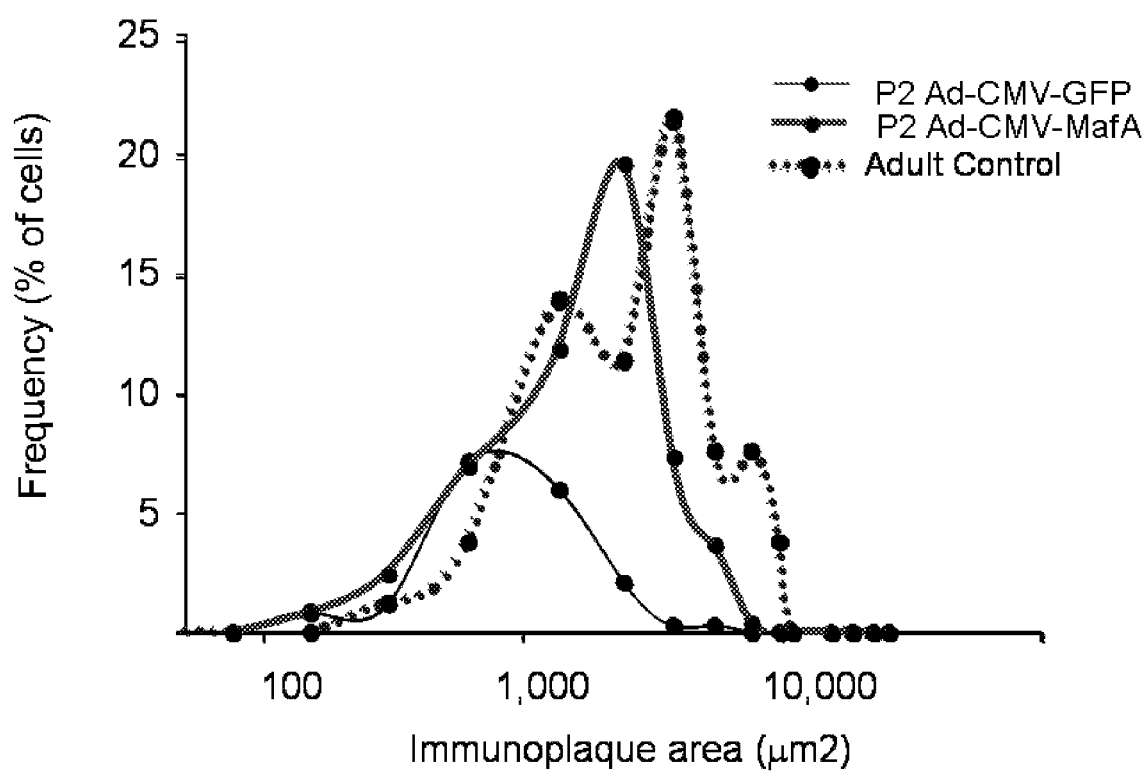
FIG. 4F is a line graph showing an increase in functional beta cells in MafA overexpressing P2 β cells compared to P2 β cells overexpressing GFP from one of the experiments. The MafA overexpressing cells approach the adult level of frequency of functional beta cells N=3.

As shown in FIG. 4B, uninfected and Adv-GFP infected P2 controls responded poorly to stimulatory glucose concentrations. In contrast, robust insulin secretion was observed in uninfected and Adv-GFP infected adult cells; in response to a change from 2.8 mM glucose to 16.8 mM, insulin secretion increased significantly. However, as shown in FIG. 4C, there was no change in insulin content coinciding with the increase in glucose responsiveness after overexpression of MafA. Importantly, Adv-MafA infected P2 cells also had a significantly increased secretion index, due to both increases in the percentage of secreting cells and in the immunoplaque area (see FIGS. 4D-E). Finally, as shown in FIG. 4F, there was a significant increase in functional mature beta cells in MafA overexpressing P2 beta cells compared to P2 beta cells over-expressing GFP. The MafA overexpressing cells approached the adult level of frequency of functional beta cells.

These data strongly support that reduced expression/activity of MafA in neonatal islets contributes to the immaturity of neonatal beta-cells and further suggest that the process of maturation of immature insulin-producing cells continues through the neonatal period. Conversely, these data support that an increase in MafA promotes glucose-induced insulin secretion.

Example 3

T3 Thyroid Hormone Promotes Beta Cell Maturation

Experimentation was performed to identify physiological stimuli that regulate MafA expression. Thyroxine was selected as a candidate because its levels are low at birth and increase progressively, peak at P15, and attain adult levels by P21.

Figure 5A:
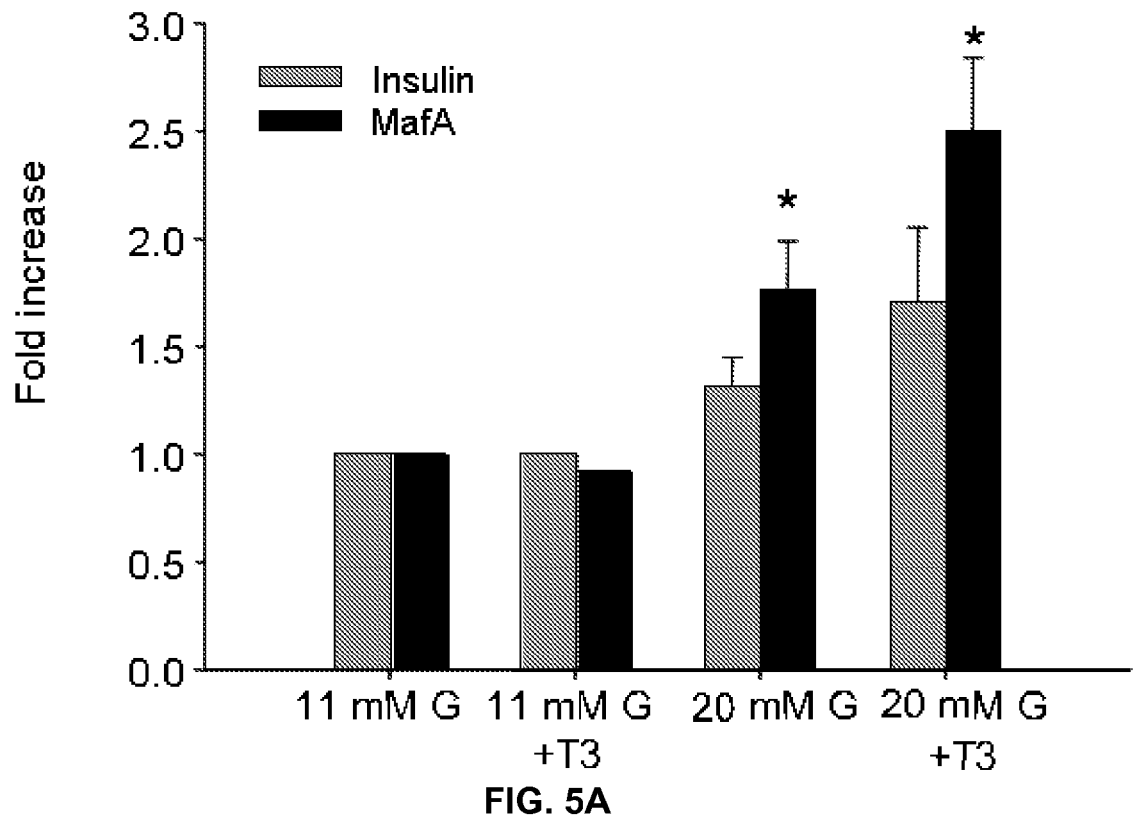
FIG. 5A is a histogram showing that Thyroid hormone (T3) and glucose separately and together increase MafA transcription in P7 islets cultured in the presence of glucose and T3 at 0.015 nM in charcoal stripped (CS)-FBS for four days. Data was obtained using quantitative PCR.

To analyze the role of thyroid hormone during postnatal development of the endocrine pancreas, dispersed P7 islets were cultured with the two changing physiological stimuli identified so far glucose (11 mM and 20 mM) and tri-iodothyronine (T3 at $10^{-11}$ M in charcoal-stripped fetal bovine serum (CS-FBS)), and after 4 days MafA and insulin transcription were assessed. Both stimuli separately and together significantly increased MafA mRNA (see FIG. 5A) and insulin mRNA, suggesting that these could be in vivo regulators of MafA expression and hence of beta cell maturation. In one experiment in which insulin secretion was evaluated by RHPA in P7 cells cultured for 4 days with thyroid hormone; an increase in insulin secretion in response to 16.8 mM glucose was seen in T3 treated cells. These results support that thyroid hormone and other physiological stimuli regulate MafA expression and accelerate beta cell maturation.

Figure 5B:
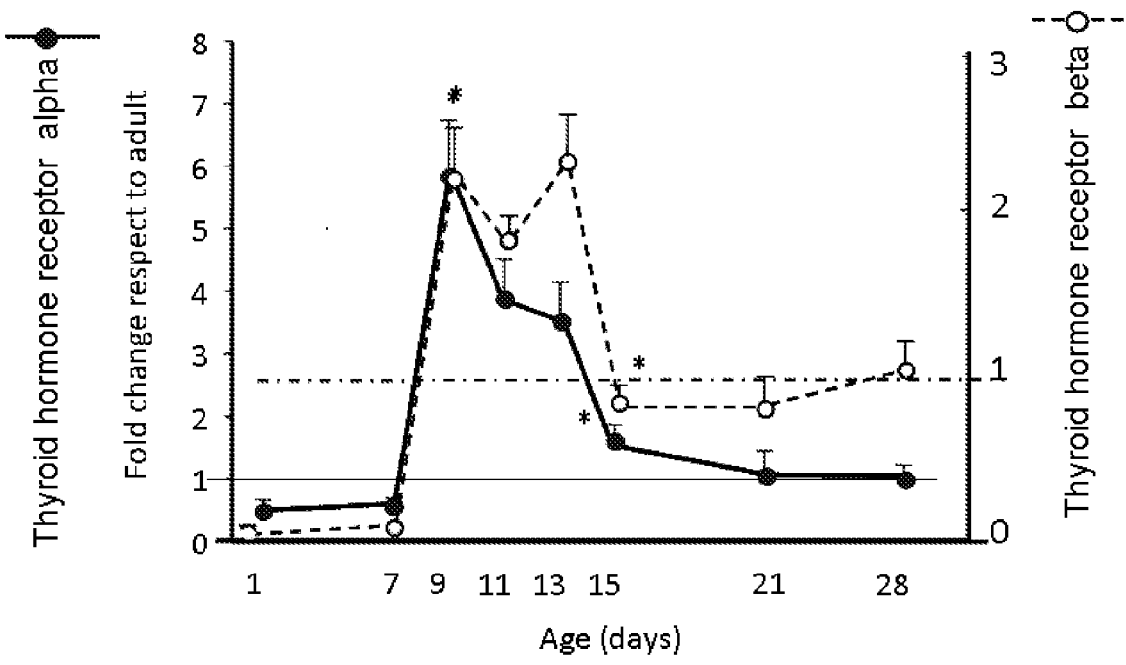
FIG. 5B is a line graph showing thyroid hormone receptor α1 (solid line and circles) and β1 (open line and circles) in neonatal islets. Each data point represents 4-5 samples.

To test the feasibility of thyroid hormone actions upon neonatal beta cells we immunostained for the thyroid receptors isoforms α1 and 2 and beta1. Paraffin sections over the time course were immunostained in parallel and photographed confocally at the same settings to allow comparison of protein expression. Using this method, as shown in FIG. 5B, a transient increase of the thyroid receptor alpha between P7 and P10 was observed; this receptor was specifically localized in the beta cell nuclei. Thyroid receptor beta also increased at P7, however its localization then was mainly cytoplasmic; we did not observe its presence in beta cell nuclei until P15, suggesting an age dependent nucleo-cytoplasmic translocation. The observation that two isoforms of thyroid receptors are present on beta cells with their changing levels and cellular localization supports that thyroid hormone has a role during postnatal development of the endocrine pancreas.

To further explore this idea, dispersed P8 islets were cultured with two changing physiological stimuli identified so far glucose (11 mM and 20 mM) and tri-iodothyronine (T3) at a concentration of $10^{-11}$ M (T-11; gray bars) or with 0.015 nM T3 (T-9) in charcoal-stripped fetal bovine serum (CS-FBS); after 4 days transcription levels of MafA and the MafA targets Ins2, GLP1R, PCSK1, PC, and LDH-A were assessed.

Figure 5C:
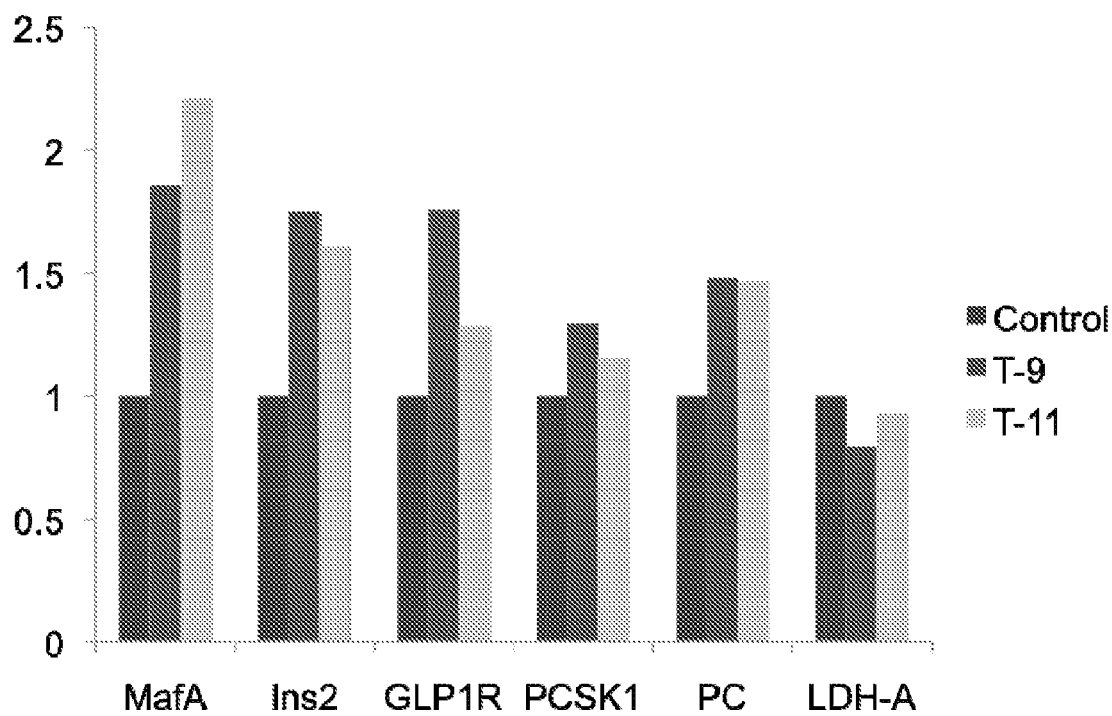
FIG. 5C is a histogram showing expression of MafA and the MafA targets Ins2, GLP1R, PCSK1, PC, and LDH-A in dispersed P8 islets cultured for four days with glucose (11 mM and 20 mM and T3 thyroid hormone at a concentration of $10^{-11}$ M (T-11; gray bars) or with 0.015 nM T3 (T-9).

As shown in FIG. 5C, both glucose and T3 significantly increased MafA and insulin mRNA strongly suggesting that they could be in vivo regulators of MafA expression and beta cell maturation. When P8 islets were cultured for 4 days with 0.015 nM T3 (T-9), MafA mRNA increased 2.5 fold and insulin mRNA 71% compared with control cultured islets.

Figure 6A:
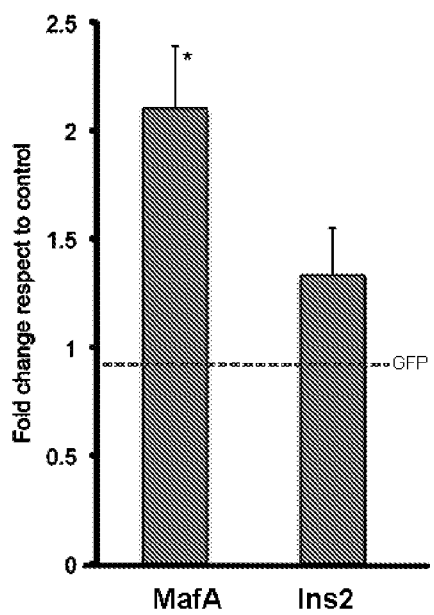
FIG. 6A is a bar graph showing fold change in MafA and Insulin mRNA levels in P8 islets after treatment with T3.
Figure 6B:
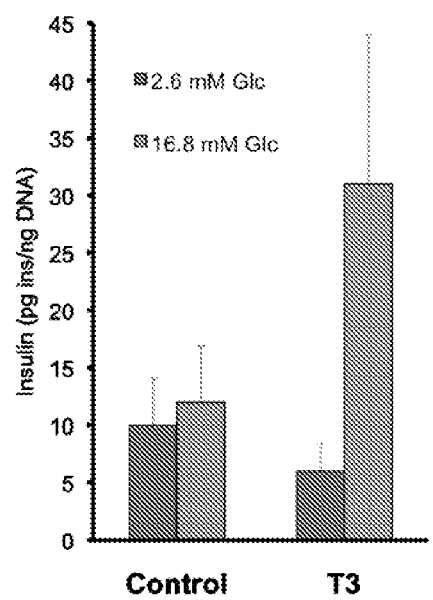
FIG. 6B is a histogram showing glucose-stimulated insulin secretion in P8 islets cultured for four days with T3 at $10^{-11}$ M and challenged with 2.6 mM or 16.8 mM glucose. using static incubation. n=4.
Figure 7A:
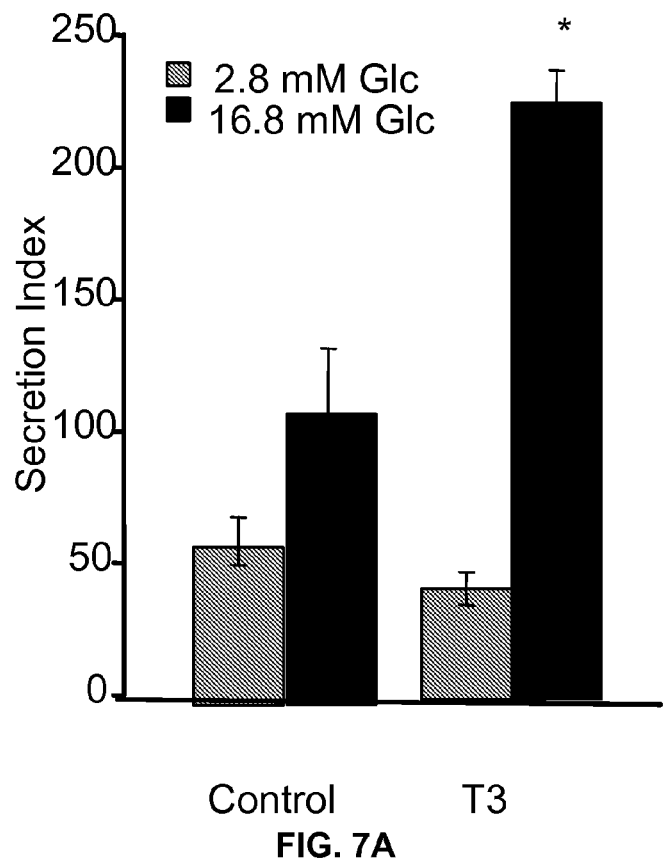
FIGS. 7A and 7B are a pair of bar graphs showing insulin secretion index (7A) and percentage of secreting cells (7B) as assessed by RHPA. These data show T3 increases insulin secretion in the presence 16.8 mM glucose from P7 cells treated with T3 compared to untreated control cells. n=3; *p<0.01
Figure 7B:
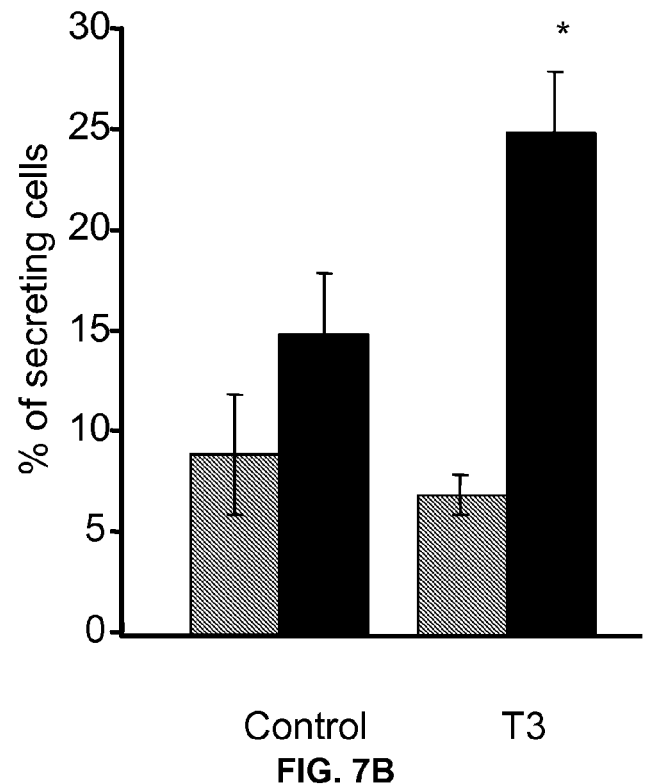
Figure 8A:
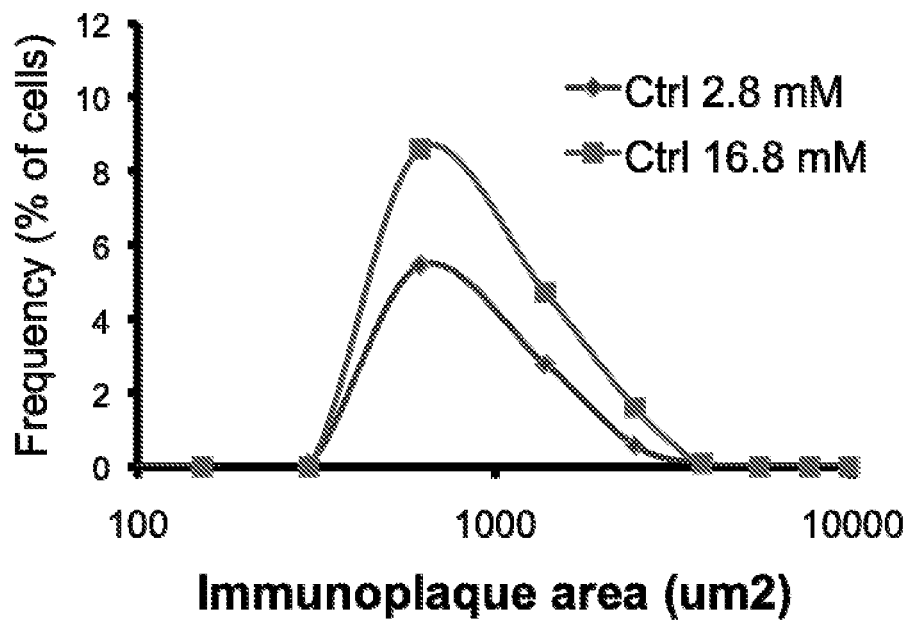
FIGS. 8A and 8B are line graphs showing β cell glucose responsiveness in 2.8 or 16.8 mM glucose in control cells (8A) or cells treated with T3 (8B) in one of the three RHPA experiments.; *p<0.01
Figure 8B:
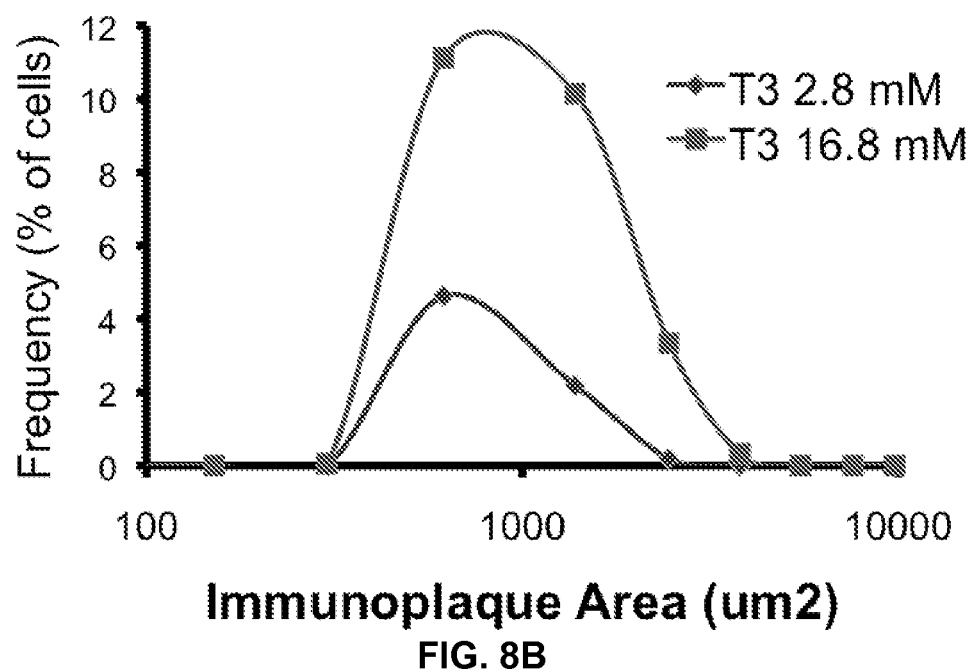
Figure 9:
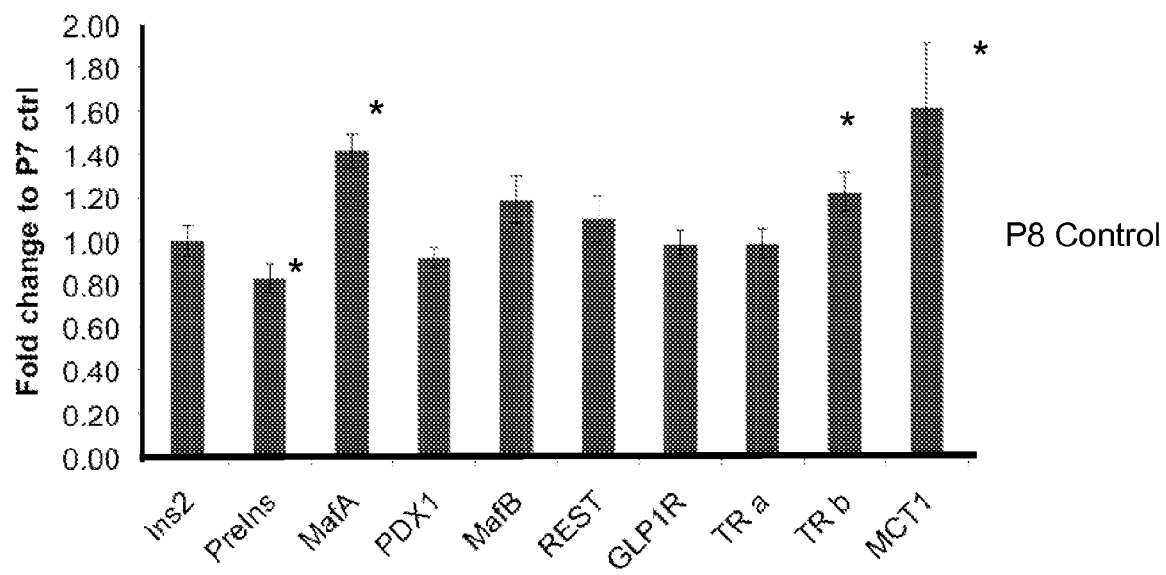
FIG. 9 is a bar graph showing fold change in levels of gene expression in P8 islet cells treated with T3 as compared to control untreated cells. n=16-17; *p<0.05

Similar results were found in static incubation experiments were performed with P7 dispersed islets cultured in the presence (or absence) of $10^{-11}$ M T3 for four days. mRNA levels for MafA and Ins2 were evaluated using real-time PCR. The results, shown in FIG. 6A, demonstrate that in vitro T3 increased MafA mRNA levels by about two-fold. Glucose-stimulated insulin secretion was also evaluated in these cells in static incubation system by measuring secreted insulin using ELISA, and shown to be significantly increased in cells treated with T3 (see FIG. 6B). To further evaluate insulin secretion in these cells, P8 islets were dispersed and then cultured for 4 days with and without $10^{-11}$ M T3, and a reverse hemolytic plaque assay (RHPA) was used to evaluate insulin secretion from single beta cells. The results showed a marked increase in insulin secretion index (FIG. 7A) and in the percentage of insulin secreting cells (FIG. 7B), indicating that in vitro T3 increased secretion index by increasing the number of glucose-responsive cells. FIGS. 8A-8B show beta cell glucose responsiveness in 2.8 or 16.8 mM glucose in control cells (8A) or cells treated with T3 (8B) in one of the three RHPA experiments. Finally, the effect of T3 on transcription of a number of genes was evaluated using quantitative PCR; the results, shown in FIG. 9, demonstrate that T3 significantly increases transcription of MafA, TRb and MCT1.

The data presented herein indicate that at the time of first increase in MafA expression between P7 and P9, serum T4 levels are rising to its peak at P15. Concurrently, expression for thyroid receptors TR-alpha and beta are increasing both at mRNA and protein levels. Additionally, these receptors become localized to the nuclei. As demonstrated in this example, T3 in culture increased MafA mRNA levels in P7 islets, and enhanced glucose-induced insulin secretion of functionally immature β-cells as measured both by static incubation and reverse hemolytic plaque assay.

These observations, together with those shown in Example 2, indicate that thyroid hormones (e.g., T3) are likely physiological regulators of MafA expression and the resultant functional maturation of beta-cells. Thus, administration of thyroid receptor (TR) pathway agonists (e.g., T3) promotes beta cell maturation, likely by increasing MafA expression levels, in insulin expressing immature beta cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing an enriched population of mature, glucose-responsive insulin secreting cells, the method comprising:
    providing an initial cell population comprising at least 10% pancreatic islet-isolated insulin-expressing immature beta cells, wherein the cells do not substantially secrete insulin in response to glucose; and
    contacting the initial population of immature beta cells with triiodothyronine (T3) thyroid hormone or an analog thereof under conditions and for a time sufficient to induce maturation of at least some of the cells into mature cells that secrete insulin in the presence of glucose in vitro,
    thereby providing an enriched population of mature, glucose-responsive insulin secreting cells.

2. A method for providing an enriched population of mature, glucose-responsive insulin secreting cells, the method comprising:
    providing an initial cell population comprising at least 10% pancreatic islet-isolated insulin-expressing immature beta cells, wherein the cells secrete a level of insulin in the presence of glucose in vitro; and
    contacting the initial population of cells with triiodothyronine (T3) thyroid hormone or an analog thereof under conditions and for a time sufficient to induce maturation of at least some of the cells into mature cells that secrete a second level of insulin in the presence of glucose in vitro, wherein the second insulin level is greater than the first level,
    thereby providing an enriched population of mature, glucose-responsive insulin secreting cells.

3. The method of claim 2, wherein the initial population of insulin-expressing cells is provided by a method comprising:
    providing a beta cell progenitor; and
    differentiating the progenitor cell into a population comprising insulin-expressing cells.

4. The method of claim 2, wherein the initial population of insulin-expressing cells secretes substantially no insulin in a glucose responsive manner.

5. The method of claim 2, wherein the initial population of insulin-expressing immature beta cells secretes substantially less insulin in a glucose responsive manner than is secreted by a comparable population of mature beta cells.

6. The method of claim 2, wherein the initial population of insulin-expressing cells expresses insulin, but does not substantially express MafA.

7. The method of claim 2, wherein the initial population of insulin-expressing cells is an enriched population of immature beta cells.

8. The method of claim 2, wherein the analog of T3 is selected from the group consisting of T4 thyroid hormone, thyromimetics, TRbeta selective agonist-GC-1, GC-24, 4-Hydroxy-PCB 106, MB07811, MB07344, 3,5-diiodothyropropionic acid (DITPA); GC-1; 3-Iodothyronamine (T(1) AM) and 3,3',5-triiodothyroacetic acid (Triac); KB-2115 and KB-141; thyronamines; SKF L-94901; DIBIT; 3'-AC-T2; tetraiodothyroacetic acid (Tetrac) and triiodothyroacetic acid (Triac), 3,3',5'-triiodothyronine (rT3), 3,3'-diiodothyronine (3,3'-T2), 3,5-diiodothyronine (T2), 3-iodothyronamine (T1AM) and thyronamine (T0AM), 3,5,3'-triiodothyropropionic acid (Triprop), 3,5-dibromo-3-pyridazinone-l-thyronine (L-940901), N-[3,5-dimethyl-4-(4'-hydroxy-3'-isopropylphenoxy)-phenyl]-oxamic acid (CGS 23425), 3,5-dimethyl-4[(4'-hydroxy-3'-isopropylbenzyl)-phenoxy]acetic acid (GC-1), 3,5-dichloro-4[(4-hydroxy-3-isopropylphenoxy)phenyl]acetic acid (KB-141), and 3,5-diiodothyropropionic acid (DITPA).

9. The method of claim 2, wherein the initial population of insulin-expressing cells express one or more, two or more, three or more, or all four of MMP2, CKI9, SPD, and Frizzled 2.

10. A method of treating or reducing the risk of developing diabetes in a subject, the method comprising:
    administering to a subject an enriched population of mature, glucose-responsive insulin secreting cells produced by the method of claim 2.

* * * * *